United States Patent
Hondalus et al.

(10) Patent No.: US 7,297,339 B2
(45) Date of Patent: Nov. 20, 2007

(54) RHODOCOCCUS EQUI MUTANTS AND VACCINES COMPRISING SAME

(75) Inventors: Mary Hondalus, Crawford, GA (US); Shruti Jain, Durham, NC (US); Joseph Ashour, New York, NY (US)

(73) Assignee: Presidents and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/036,797

(22) Filed: Jan. 14, 2005

(65) Prior Publication Data

US 2005/0276817 A1 Dec. 15, 2005

Related U.S. Application Data

(63) Continuation of application No. PCT/US03/22101, filed on Jul. 14, 2003.

(60) Provisional application No. 60/396,195, filed on Jul. 16, 2002.

(51) Int. Cl.
*A61K 39/02* (2006.01)
*C12N 1/00* (2006.01)
*C07H 21/02* (2006.01)

(52) U.S. Cl. .............. 424/235.1; 424/9.1; 424/9.2; 424/184.1; 424/234.1; 435/243; 435/252.1; 435/252.3; 435/320.1; 435/440; 435/470; 435/471; 536/23.1

(58) Field of Classification Search ............... 424/9.1, 424/9.2, 184.1, 234.1, 235.1; 435/243, 252.1, 435/252.3, 320.1, 440, 470, 471; 536/23.1
See application file for complete search history.

(56) References Cited

OTHER PUBLICATIONS

Hondalus and Mosser; "Survival and Replication of *Rhodococcus equi* in Macrophages"; 1994; *Infection and Immunity*; 62(10): 4167-4175.

Hondalus; "Pathogenesis and virulence of *Rhodococcus equi*"; 1997; *Veterinary Microbiology*; 56: 257-268.

Giguere, et al.; "Role of the 85-Kilobase Plasmid and Plasmid-Encoded Virulence-Associated Protein A in Intracellular Survival and Virulence of *Rhodococcus equi*"; 1999; *Infection and Immunity*; 67(7): 3548-3557.

Darrah, et al.; "Cooperation between Reactive Oxygen and Nitrogen Intermediates in Killing of *Rhodococcus equi* by Activated Macrophages"; 2000; *Infection and Immunity*; 68(6): 3587-3593.

International Search Report for PCT/US003/22101 dated Mar. 9, 2004.

*Primary Examiner*—Rodney P Swartz
(74) *Attorney, Agent, or Firm*—Edwards Angell Palmer & Dodge LLP; Kathleen Williams

(57) ABSTRACT

Mutant strains of *Rhodococcus equi* are disclosed, and vaccines comprising same.

6 Claims, 30 Drawing Sheets

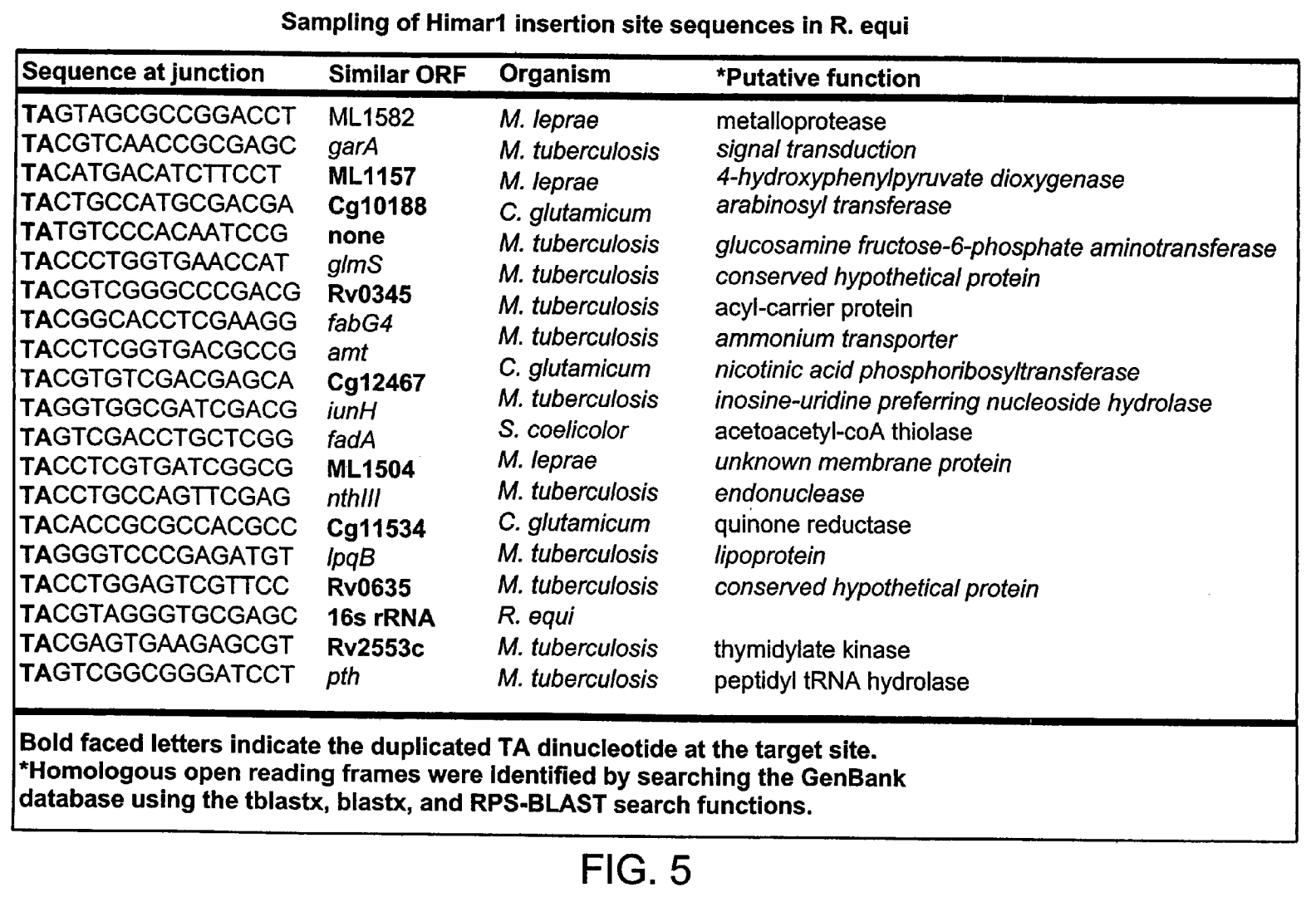

Sampling of Himar1 insertion site sequences in R. equi

| Sequence at junction | Similar ORF | Organism | *Putative function |
|---|---|---|---|
| TAGTAGCGCCGGACCT | ML1582 | *M. leprae* | metalloprotease |
| TACGTCAACCGCGAGC | garA | *M. tuberculosis* | sign

Capsular phenotypes found in morphology screen

Wild type R. equi

D1

D2

Sequence Alignment of Vap proteins

FIG. 13

| FIG. 13A |
|----------|
| FIG. 13B |

FIG. 13A

```
VapA  ----------------------------------MKTLHKTVSKAIAATAVAAAAMIPAGVANATVLD-SGSSSAILN    44
VapC  -----------------------------------------MFR----VGRPSKSIAVVASVLCFLALGGTARANVVAPSAWGGAQSA    43
VapD  ----------------------------------------MVRARAFGRLFTFLLAVIATVSMGGANAQELAGTKTSDAALL    44
VapE  MTTVHKKASKAIAFTVALRLPFAGTAVALVLIALTIVAAPTGIAGAREIGAQAWPASQLE    60
VapF  ---------------------------------MIEYAWYGPSIQSNRCCGDCPILLALGGHRTCRLATPSAWVGTPSA    46
VapG  ----------------------------------------MSVR----TLLAATLVAGISVLAPAGIANAETSMVSTTAASSVE    40
VapH  -----------------------------MNLSKTTRKFLSRTAVPATFVMALTVPWGCAAPPPLPDGPTHDLPTW    47

VapA  SGAGSGIVGSGSYDSSTTSLNLQKDEPNGRASDTAGQEQQYDVHGDVISAVVYQRFHVFG    104
VapC  ADKEGEGVTLGGVGVLRPHN-------------KDADEQYTVHGVVVSALFYNHLRISV    89
VapD  SGNKAAIP----------------------EDKEYDVSGRVVSALVYQYFIVTV    76
VapE  SGLAVSGNPVGVHDVRMAV---HDDSTHTREFKEDDSEKQYPVHGFASSFIFYQTVSIII    117
VapF  AGK--------VLPPIN---------NNADEQYAVHGVVFSAVFYNHVRISV    81
VapG  H----AAN---TYDFAEAK---SGSSIPAKVAAEQAN--SYSVHGLVTSLAVYQHFSLTV    88
VapH  REEGANYSDGTMLVRASSN-----------FLEPSTHSDSGQQQWTVQGVLASAIVYQRLKLNV    100
```

**Growth of *R. equi vap* locus mutant in mice**

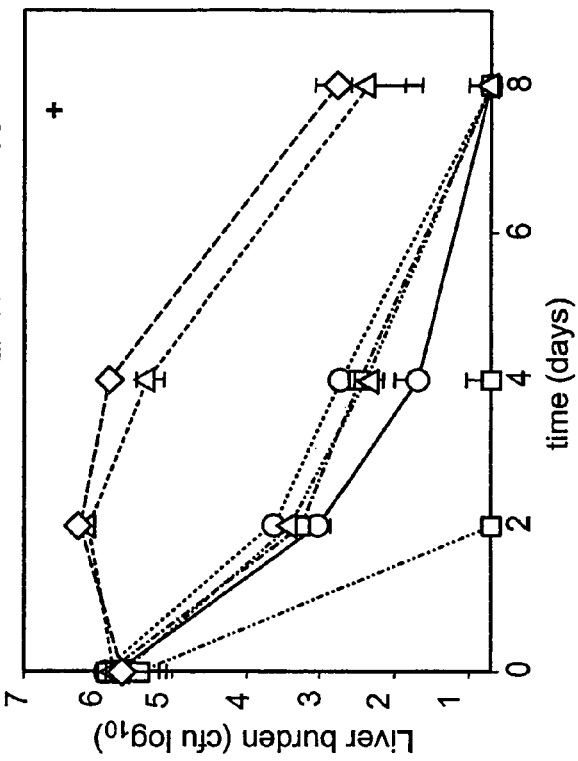
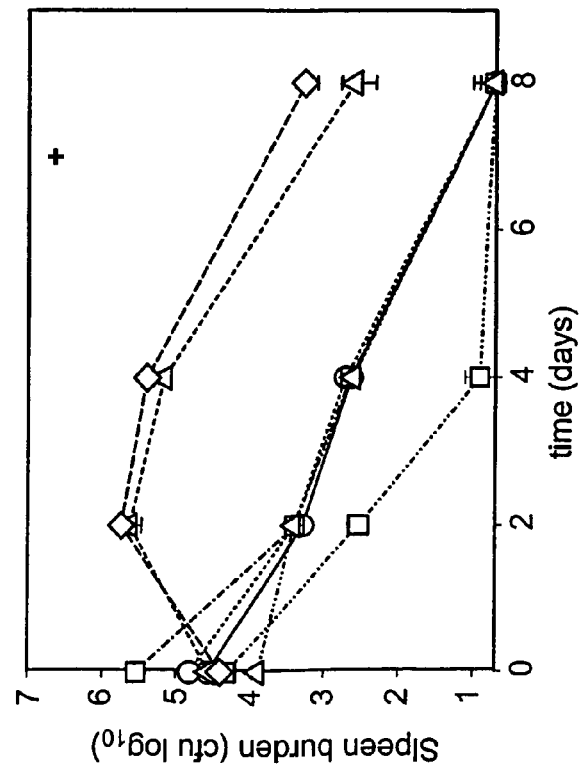

Southern Blot analysis of *R. equi vap* locus and *vapA* mutants

**Western blot analysis showing complementation of *R. equi vapA* mutant**

SEQUENCE LISTING

<160> NUMBER OF SEQ ID NOS: 37

<210> SEQ ID NO 1
<211> LENGTH: 20
<212> TYPE: DNA
<213> ORGANISM: Artificial
<220> FEATURE:
<223> OTHER INFORMATION: Forward PCR primer

<400> SEQUENCE: 1
ttcaccgatc cggaggaact                                                   20

<210> SEQ ID NO 2
<211> LENGTH: 20
<212> TYPE: DNA
<213> ORGANISM: Artificial
<220> FEATURE:
<223> OTHER INFORMATION: Reverse PCR primer

<400> SEQUENCE: 2
tccccggtct ctagaattca                                                   20

<210> SEQ ID NO 3
<211> LENGTH: 20
<212> TYPE: DNA
<213> ORGANISM: Artificial
<220> FEATURE:

<223> OTHER INFORMATION: Aprimycin forward PCR primer

<400> SEQUENCE: 3
tcatcggtca gcttctcaac                                               20

<210> SEQ ID NO 4
<211> LENGTH: 20
<212> TYPE: DNA
<213> ORGANISM: Artificial
<220> FEATURE:
<223> OTHER INFORMATION: Apramycin reverse PCR primer

<400> SEQUENCE: 4
cacagcagtg gtcattctcg                                               20

<210> SEQ ID NO 5
<211> LENGTH: 25
<212> TYPE: DNA
<213> ORGANISM: Artificial
<220> FEATURE:
<223> OTHER INFORMATION: vapA forward PCR primer

<400> SEQUENCE: 5
ggcgtcgctg ggcccaccgt tcttg                                         25

<210> SEQ ID NO 6
<211> LENGTH: 26
<212> TYPE: DNA
<213> ORGANISM: Artificial
<220> FEATURE:
<223> OTHER INFORMATION: vapA reverse PCR primer

<400> SEQUENCE: 6
tacgtgcagc gaattcggcg ttgtgc                                        26

<210> SEQ ID NO 7
<211> LENGTH: 20
<212> TYPE: DNA
<213> ORGANISM: Artificial
<220> FEATURE:
<223> OTHER INFORMATION: Forward PCR primer

<400> SEQUENCE: 7
atcatcaggg ctcgacggga                                               20

<210> SEQ ID NO 8
<211> LENGTH: 20
<212> TYPE: DNA
<213> ORGANISM: Artificial
<220> FEATURE:
<223> OTHER INFORMATION: Reverse PCR primer

<400> SEQUENCE: 8
caagttgtcc tcgctgccac                                               20

<210> SEQ ID NO 9
<211> LENGTH: 30
<212> TYPE: DNA
<213> ORGANISM: Artificial
<220> FEATURE:
<223> OTHER INFORMATION: Reverse PCR primer

<400> SEQUENCE: 9
gctcttagcg gcccggaaac gtcctcgaaa                                    30

```
<210> SEQ ID NO 10
<211> LENGTH: 30
<212> TYPE: DNA
<213> ORGANISM: Artificial
<220> FEATURE:
<223> OTHER INFORMATION: Reverse PCR primer

<400> SEQUENCE: 10
cttggccatt gcgaagtgat tcctccggat                               30

<210> SEQ ID NO 11
<211> LENGTH: 16
<212> TYPE: DNA
<213> ORGANISM: Mycobacterium leprae

<400> SEQUENCE: 11
tagtagcgcc ggacct                                              16

<210> SEQ ID NO 12
<211> LENGTH: 16
<212> TYPE: DNA
<213> ORGANISM: Mycobacterium tuberculosis

<400> SEQUENCE: 12
tacgtcaacc gcgagc                                              16

<210> SEQ ID NO 13
<211> LENGTH: 16
<212> TYPE: DNA
<213> ORGANISM: Mycobacterium leprae

<400> SEQUENCE: 13
tacatgacat cttcct                                              16

<210> SEQ ID NO 14
<211> LENGTH: 16
<212> TYPE: DNA
<213> ORGANISM: C. glutamicum

<400> SEQUENCE: 14
tactgccatg cgacga                                              16

<210> SEQ ID NO 15
<211> LENGTH: 16
<212> TYPE: DNA
<213> ORGANISM: Mycobacterium tuberculosis

<400> SEQUENCE: 15
tatgtcccac aatccg                                              16

<210> SEQ ID NO 16
<211> LENGTH: 16
<212> TYPE: DNA
<213> ORGANISM: Mycobacterium tuberculosis

<400> SEQUENCE: 16
taccctggtg aaccat                                              16

<210> SEQ ID NO 17
<211> LENGTH: 16
<212> TYPE: DNA
<213> ORGANISM: Mycobacterium tuberculosis

<400> SEQUENCE: 17
```

```
tacgtcgggc cgacg                                                    16

<210> SEQ ID NO 18
<211> LENGTH: 16
<212> TYPE: DNA
<213> ORGANISM: Mycobacterium tuberculosis

<400> SEQUENCE: 18
tacggcacct cgaagg                                                   16

<210> SEQ ID NO 19
<211> LENGTH: 16
<212> TYPE: DNA
<213> ORGANISM: C. glutamicum

<400> SEQUENCE: 19
tacctcggtg acgccg                                                   16

<210> SEQ ID NO 20
<211> LENGTH: 16
<212> TYPE: DNA
<213> ORGANISM: Mycobacterium tuberculosis

<400> SEQUENCE: 20
tacgtgtcga cgagca                                                   16

<210> SEQ ID NO 21
<211> LENGTH: 16
<212> TYPE: DNA
<213> ORGANISM: S. coelicolor

<400> SEQUENCE: 21
taggtggcga tcgacg                                                   16

<210> SEQ ID NO 22
<211> LENGTH: 16
<212> TYPE: DNA
<213> ORGANISM: Mycobacterium leprae

<400> SEQUENCE: 22
tagtcgacct gctcgg                                                   16

<210> SEQ ID NO 23
<211> LENGTH: 16
<212> TYPE: DNA
<213> ORGANISM: Mycobacterium tuberculosis

<400> SEQUENCE: 23
tacctcgtga tcggcg                                                   16

<210> SEQ ID NO 24
<211> LENGTH: 16
<212> TYPE: DNA
<213> ORGANISM: C. glutamicum

<400> SEQUENCE: 24
tacctgccag ttcgag                                                   16

<210> SEQ ID NO 25
<211> LENGTH: 16
<212> TYPE: DNA
<213> ORGANISM: Mycobacterium tuberculosis

<400> SEQUENCE: 25
```

```
tacaccgcgc cacgcc                                                    16
```

<210> SEQ ID NO 26
<211> LENGTH: 16
<212> TYPE: DNA
<213> ORGANISM: Mycobacterium tuberculosis

<400> SEQUENCE: 26

```
tagggtcccg agatgt                                                    16
```

<210> SEQ ID NO 27
<211> LENGTH: 16
<212> TYPE: DNA
<213> ORGANISM: Rhodococcus equi

<400> SEQUENCE: 27

```
tacctggagt cgttcc                                                    16
```

<210> SEQ ID NO 28
<211> LENGTH: 16
<212> TYPE: DNA
<213> ORGANISM: Mycobacterium tuberculosis

<400> SEQUENCE: 28

```
tacgtagggt gcgagc                                                    16
```

<210> SEQ ID NO 29
<211> LENGTH: 16
<212> TYPE: DNA
<213> ORGANISM: Mycobacterium tuberculosis

<400> SEQUENCE: 29

```
tacgagtgaa gagcgt                                                    16
```

<210> SEQ ID NO 30
<211> LENGTH: 16
<212> TYPE: DNA
<213> ORGANISM: Mycobacterium tuberculosis

<400> SEQUENCE: 30

```
tagtcggcgg gatcct                                                    16
```

<210> SEQ ID NO 31
<211> LENGTH: 189
<212> TYPE: PRT
<213> ORGANISM: Rhodococcus equi

<400> SEQUENCE: 31

```
Met Lys Thr Leu His Lys Thr Val Ser Lys Ala Ile Ala Ala Thr Ala
1               5                   10                  15

Val Ala Ala Ala Ala Met Ile Pro Ala Gly Val Ala Asn Ala Thr
                20                  25                  30

Val Leu Asp Ser Gly Ser Ser Ala Ile Leu Asn Ser Gly Ala Gly
            35                  40                  45

Ser Gly Ile Val Gly Ser Gly Ser Tyr Asp Ser Ser Thr Thr Ser Leu
    50                  55                  60

Asn Leu Gln Lys Asp Glu Pro Asn Gly Arg Ala Ser Asp Thr Ala Gly
65                  70                  75                  80

Gln Glu Gln Gln Tyr Asp Val His Gly Asp Val Ile Ser Ala Val Val
                85                  90                  95
```

```
Tyr Gln Arg Phe His Val Phe Gly Pro Glu Gly Lys Val Phe Asp Gly
            100                 105                 110

Asp Ala Gly Gly Leu Thr Leu Pro Gly Ala Gly Ala Phe Trp Gly Thr
            115                 120                 125

Leu Phe Thr Asn Asp Leu Gln Arg Leu Tyr Lys Asp Thr Val Ser Phe
            130                 135                 140

Gln Tyr Asn Ala Val Gly Pro Tyr Leu Asn Ile Asn Phe Phe Asp Ser
145                 150                 155                 160

Ser Gly Ser Phe Leu Gly His Ile Gln Ser Gly Val Ser Thr Val
                165                 170                 175

Val Gly Val Gly Gly Ser Gly Ser Trp His Asn Ala
            180                 185
```

<210> SEQ ID NO 32
<211> LENGTH: 174
<212> TYPE: PRT
<213> ORGANISM: Rhodococcus equi

<400> SEQUENCE: 32

```
Met Phe Arg Val Gly Arg Pro Ser Lys Ser Ile Ala Val Val Ala Ser
1               5                   10                  15

Val Leu Cys Phe Leu Ala Leu Gly Gly Thr Ala Arg Ala Asn Val Val
                20                  25                  30

Ala Pro Ser Ala Trp Gly Gly Ala Gln Ser Ala Ala Asp Lys Glu Gly
            35                  40                  45

Glu Gly Val Thr Leu Gly Gly Val Gly Val Leu Arg Pro His Asn Lys
        50                  55                  60

Asp Ala Asp Glu Gln Tyr Thr Val His Gly Val Val Ser Ala Leu
65                  70                  75                  80

Phe Tyr Asn His Leu Arg Ile Ser Val Asp Gly Gly Met Thr Phe Asp
                85                  90                  95

Gly Asp Gly Gly Gly Leu Ser Thr Pro Gly Gly Ala Leu Trp Gly
            100                 105                 110

Thr Leu Thr Thr Ser Asp Leu Gln Gln Leu Tyr Asp Glu Thr Ala Ser
            115                 120                 125

Phe Glu Cys Asn Ala Val Gly Pro Tyr Leu Asn Ile Asn Phe Tyr Asp
            130                 135                 140

Ser Tyr Gly Arg Ile Leu Ala Ser Val Gln Ala Gly Val Ser Thr
145                 150                 155                 160

Met Ile Gly Ile Gly Gly Gly Asn Gly Arg Trp His Leu Val
                165                 170
```

<210> SEQ ID NO 33
<211> LENGTH: 164
<212> TYPE: PRT
<213> ORGANISM: Rhodococcus equi

<400> SEQUENCE: 33

```
Met Val Arg Ala Arg Ala Phe Gly Arg Leu Phe Thr Phe Leu Leu Ala
1               5                   10                  15

Val Ala Val Ile Ala Thr Val Ser Met Gly Gly Ala Asn Ala Gln Glu
                20                  25                  30

Leu Ala Gly Thr Lys Thr Ser Asp Ala Ala Leu Leu Ser Gly Asn Lys
            35                  40                  45

Ala Ala Ile Pro Glu Asp Lys Glu Tyr Asp Val Ser Gly Arg Val Val
        50                  55                  60
```

```
Ser Ala Leu Val Tyr Gln Tyr Phe Ile Val Thr Val Asp Asp Ala Glu
 65                  70                  75                  80

Asp Lys Lys Gly Lys Thr Phe Gln Gly Asp Ala Gly Val Thr Ile
                 85                  90                  95

Pro Gly Val Asp Phe Phe Trp Gly Thr Leu His Thr Pro Asp Leu Glu
                100                 105                 110

Lys Leu Tyr Ser Asp Thr Val Ser Phe Gln Tyr Asn Ala Ala Ala Thr
                115                 120                 125

Phe Leu Asn Ile Asn Phe Phe Asp Ser Lys Gly Glu Arg Leu Gly Tyr
        130                 135                 140

Val Leu Ala Gly Ala Ala Gly Thr Val Ser Gly Ile Gly Gly Gly Thr
145                 150                 155                 160

Gly Gly Trp Glu

<210> SEQ ID NO 34
<211> LENGTH: 206
<212> TYPE: PRT
<213> ORGANISM: Rhodococcus equi

<400> SEQUENCE: 34

Met Thr Thr Val His Lys Lys Ala Ser Lys Ala Ile Ala Phe Thr Val
1                   5                  10                  15

Ala Leu Arg Leu Pro Phe Ala Gly Thr Ala Val Ala Leu Val Leu Ile
                 20                  25                  30

Ala Leu Thr Ile Val Ala Ala Pro Thr Gly Ile Ala Gly Ala Arg Glu
                 35                  40                  45

Ile Gly Ala Gln Ala Trp Pro Ala Ser Gln Leu Glu Ser Gly Leu Ala
        50                  55                  60

Val Ser Gly Asn Pro Val Gly Val His Asp Val Arg Met Ala Val His
65                  70                  75                  80

Asp Asp Ser Thr His Thr Arg Glu Phe Lys Glu Asp Asp Ser Glu Lys
                 85                  90                  95

Gln Tyr Pro Val His Gly Phe Ala Ser Ser Phe Ile Phe Tyr Gln Thr
                100                 105                 110

Val Ser Ile Ile Ile Asp Asp Gly Arg Gly Gly Pro Gly Lys Thr
                115                 120                 125

Phe Glu Gly Glu Ala Gly Gly Ile Thr Thr Pro Gly Ala Ala Gly Tyr
        130                 135                 140

Ala Gly Val Leu Phe Thr Ser Asp Leu Glu Arg Leu Tyr Arg Glu Thr
145                 150                 155                 160

Val Ser Phe Glu Tyr Asn Ala Val Gly Pro Tyr Leu Asn Ile Asn Leu
                165                 170                 175

Phe Ala Gly Asp Gly Gly Leu Leu Gly His Val Gln Ser Gly Ala Ile
                180                 185                 190

Ser Ser Leu Val Gly Ile Gly Gly Thr Gly Ala Trp Arg
                195                 200                 205

<210> SEQ ID NO 35
<211> LENGTH: 150
<212> TYPE: PRT
<213> ORGANISM: Rhodococcus equi

<400> SEQUENCE: 35

Met Ile Glu Tyr Ala Trp Tyr Gly Pro Ser Ile Gln Ser Asn Arg Cys
1                   5                  10                  15

Cys Gly Asp Cys Pro Ile Leu Leu Ala Leu Gly Gly His Arg Thr Cys
```

-continued

```
                    20                  25                  30
Arg Leu Ala Thr Pro Ser Ala Trp Val Gly Thr Pro Ser Ala Ala Gly
            35                  40                  45

Lys Val Leu Pro Pro Ile Asn Asn Ala Asp Glu Gln Tyr Ala Val
 50                  55                  60

His Gly Val Val Phe Ser Ala Val Phe Tyr Asn His Val Arg Ile Ser
 65                  70                  75                  80

Val Asp Gly Gly Met Thr Phe Asp Gly Glu Gly Gly Leu Ser Thr
                85                  90                  95

Pro Gly Gly Gly Ala Leu Trp Gly Asn Leu Met Thr Ser Asp Leu Leu
            100                 105                 110

Cys Ser Ser Tyr Thr Thr Lys Leu Arg Arg Ser Asn Val Ile Trp Pro
            115                 120                 125

Val Ser Lys Asp Gln Leu Leu Arg Gln Leu Trp Trp His Ser Trp Glu
            130                 135                 140

Cys Ser Arg Glu Arg Cys
145                 150

<210> SEQ ID NO 36
<211> LENGTH: 172
<212> TYPE: PRT
<213> ORGANISM: Rhodococcus equi

<400> SEQUENCE: 36

Met Ser Val Arg Thr Leu Leu Ala Ala Thr Leu Val Ala Gly Ile Ser
  1               5                  10                  15

Val Leu Ala Pro Ala Gly Ile Ala Asn Ala Glu Thr Ser Met Val Ser
             20                  25                  30

Thr Thr Ala Ala Ser Ser Val Glu His Ala Ala Asn Thr Tyr Asp Phe
         35                  40                  45

Ala Glu Ala Lys Ser Gly Ser Ser Ile Pro Ala Lys Val Ala Ala Glu
     50                  55                  60

Gln Ala Asn Ser Tyr Ser Val His Gly Leu Val Thr Ser Leu Ala Val
 65                  70                  75                  80

Tyr Gln His Phe Ser Leu Thr Val Glu Gly Glu Lys Thr Phe Thr
             85                  90                  95

Gly Asp Ser Gly Gly Ile Ser Ile Pro Gly Val Ala Val Leu Glu Gly
            100                 105                 110

Thr Leu Phe Thr Glu Asp Leu Gln His Leu Tyr Ser Asp Thr Val Ser
            115                 120                 125

Phe Glu Tyr Asn Ala Val Gly Pro Tyr Leu Asn Ile Asn Phe Phe Asp
            130                 135                 140

Ser His Gly Thr Leu Leu Gly His Val Gln Ser Gly Ser Ile Gly Thr
145                 150                 155                 160

Val Ser Gly Ile Gly Gly Gly Thr Gly Gly Trp Gln
                165                 170

<210> SEQ ID NO 37
<211> LENGTH: 188
<212> TYPE: PRT
<213> ORGANISM: Rhodococcus equi

<400> SEQUENCE: 37

Met Asn Leu Ser Lys Thr Thr Arg Lys Phe Leu Ser Arg Thr Ala Val
  1               5                  10                  15

Pro Ala Thr Phe Val Met Ala Leu Thr Val Pro Trp Gly Cys Ala Ala
```

-continued

```
            20                  25                  30
Pro Pro Pro Leu Pro Asp Gly Pro Thr His Asp Leu Pro Thr Trp Arg
        35                  40                  45

Glu Glu Gly Ala Asn Tyr Ser Asp Gly Thr Met Leu Val Arg Ala Ser
    50                  55                  60

Ser Asn Phe Leu Glu Pro Ser Thr His Ser Asp Ser Gly Gln Gln Gln
65                  70                  75                  80
Trp Thr Val Gln Gly Val Leu Ala Ser Ala Leu Val Tyr Gln Arg Leu
                85                  90                  95
Lys Leu Asn Val Glu Gly Gly Glu Thr Phe Glu Gly Tyr Ala Gly Gly
            100                 105                 110
Leu Ser Phe Pro Gly Gly Ala Met Val Trp Gly Thr Leu Phe Thr Asp
        115                 120                 125

Asn Ile Gln Arg Leu Tyr Asp Arg Thr Glu Ser Phe Glu Phe Asn Ala
    130                 135                 140
Val Gly Pro Tyr Leu Asn Val Asn Phe Phe Asp Gly His Ser Ala Ile
145                 150                 155                 160
Leu Ala Gly His Ala Gln Leu Gly Gly Val Ser Ser Val Ile Gly Ile
                165                 170                 175
Gly Gly Gly Thr Gly Thr Trp Ile Gly Asp Val Ala
            180                 185
```

RHODOCOCCUS EQUI MUTANTS AND VACCINES COMPRISING SAME

This application is a Continuation of PCT/US2003/022101 which was filed on 14 Jul. 2003 which claims priority under 35 U.S.C. § 119 to U.S. Provisional Application Ser. No. 60/396,195 which was filed on 16 Jul. 2002, the entirety of each of which is incorporated herein by reference.

BACKGROUND

The facultative intracellular actinomycete, *Rhodococcus equi,* is a frequent and serious pathogen of young horses (foals) and an occasional but equally serious opportunistic pathogen of immunocompromised people [Emmons, 1991 #402]. It is one of the few bacteria capable of intramacrophage survival and replication, and thus, the study of this organism can provide insights into the biology of intracellular parasitism. The native host cell of *R. equi* is the alveolar macrophage, infected through inhalation of bacteria present in contaminated soil or dust. Pyogranulomatous pneumonia ensues which can be life threatening if appropriate long-term antibiotic therapy is not initiated or continued. Strains of *R. equi* isolated from pneumonic foals all possess a large (80.6 kb) virulence plasmid [Tkachuk-Saad, 1991 #382] [Takai, 1991 #383], the entire nucleotide sequence of which has been recently determined [Takai, 2000 #43]. This plasmid is essential for virulence, as plasmid curing attenuates the bacterium and renders it harmless to foals [Giguere, 1999 #87]. Plasmid loss yields a strain incapable of replicating intracellularly and thus, plasmid encoded factors are necessary for both intramacrophage growth and disease development in horses [Hondalus, 1994 #275][Giguere, 1999 #87]. Interestingly, the virulence plasmid is only present in a subset of *R. equi* strains isolated from humans [Takai, 1995 #236] with rhodococcal pneumonia, indicating that chromosomally derived gene products also influence the disease process.

At present, a fundamental understanding of most aspects of *R. equi* pathogenesis is lacking. Very little is known about the genetic basis for *R. equi* virulence, and no single gene product has been definitely identified as a determinate of virulence. There is therefore a need to establish the bacterial requirements for virulence, to understand why disease develops in some hosts and not others, to ascertain how best to treat rhodococcal disease when it does develop, and importantly, to construct preventative vaccines. In order to meet these goals, *R. equi* mutant strains must be created, the study of which will aid in the dissection of the molecular basis of *R. equi* pathogenesis.

Riboflavin (vitamin B2) is the precursor of the coenzymes flavin mononucleotide phosphate (FMN) and flavin adenine dinucleotide phosphate (FAD), compounds essential for growth and cell division. Riboflavin is synthesized by plants, fungi and bacteria but not by higher eukaryotes. Some bacteria are readily able to make use of exogenous sources of riboflavin, but a number, for example *E. coli* and other *Enterobacteriaceae* lack a transport system for riboflavin uptake and thus, are unable to efficiently utilize environmental sources of riboflavin. Even if a bacterium is in possession of an adequate uptake system, the mammalian environment may be so limiting in riboflavin availability that bacterial growth is prevented. Such a scenario was documented by studies of the veterinary pathogen *Actinobacillus pleuropneumoniae,* in which a riboflavin auxotroph was demonstrated to be incapable of causing disease in swine.

SUMMARY OF THE INVENTION

By transposon mutagenesis we made a mutation in a virulent strain of *R. equi* that confers riboflavin auxotrophy. In other words, the strain is unable to make the vitamin riboflavin and in order to grow, exogenous riboflavin must be added to the culture media. The mutation is in the gene encoding the putative dual functioning GTP cyclohydrolase/3,4-dihydroxy-2-butanone-4-phosphate synthase (DHBP synthase), an enzyme of the riboflavin biosynthesis pathway. We infected mice with both virulent non-auxotrophic *R. equi* and a similar number of the riboflavin mutant and monitored the in vivo grow of both strains. We discovered that riboflavin auxotrophy is indeed attenuating to *R. equi.* This is the first demonstration of an attenuation of *R. equi* due to the disruption of a metabolic gene.

The invention features an isolated mutant strain of *R. equi* that is a riboflavin auxotroph, and has reduced pathogenicity relative to a wild type strain.

The invention also features an isolated mutant strain of *R. equi* that contains a nonfunctional vapA gene, and has reduced pathogenicity relative to a wild type strain.

The invention also features vaccines that include one or the other or both of the isolated mutant strains, and a pharmaceutically acceptable carrier.

In a further aspect, the invention features a method of preventing or reducing infection by *Rhodococcus* spp., comprising administering one or more of the vaccines to a mammal at risk of infection by *Rhodococcus* spp.

The invention also features a mutant strain of *R. equi* that has a deletion in the virulence plasmid involving more than one virulence gene. The mutant strain is attenuated, and exhibits reduced pathogenicity relative to wild type strains of the same bacterium.

As used herein, an "isolated" mutant strain of *R. equi* means that cells of the mutant strain have been removed from their original environment (e.g., from the soil or from an infected mammal) and are maintained outside of that environment. For example, a naturally-occurring mutant strain present in a living animal or in the soil is not isolated, but the same mutant strain, which is separated from the living animal or soil, is isolated.

By saying that a mutant strain of *R. equi* has "reduced pathogenicity" means that, relative to a wild type strain, the mutant strain exhibits a reduction in the incidence or severity of infection by the pathogen, and/or a reduction in the incidence or severity of the resulting disease and/or a reduction in the incidence or severity of any symptom or condition resulting from infection with the pathogen as compared to that occurring in an unvaccinated, infected control animal. The determination of the reduction in these characteristics is generally made by a veterinarian.

By "nonfunctional" vapA gene, or any other vap gene, is meant that the gene in the mutant strain contains a mutation, deletion, substitution, or frame shift, etc., or alteration in the control of the gene, that renders the resulting protein non-existent or non-functional or having reduced functionality. The resulting mutant *R. equi* is attenuated, and has reduced pathogenicity, as defined above, relative to a wild type strain.

The attenuated mutant strains can be used in the preparation of vaccines to protect foals, pregnant mares and humans (e.g., immune-compromised humans, e.g., HIVinfected humans) from *Rhodococcus*-caused diseases, e.g., pneumonia caused by *Rhodococcus*.

BRIEF DESCRIPTION OF THE DRAWINGS

FIG. 5 is a table showing a number of Himar1 insertion site sequences in *R. equi* (SEQ ID Nos: 11-30).

Figures 20A, 20B:
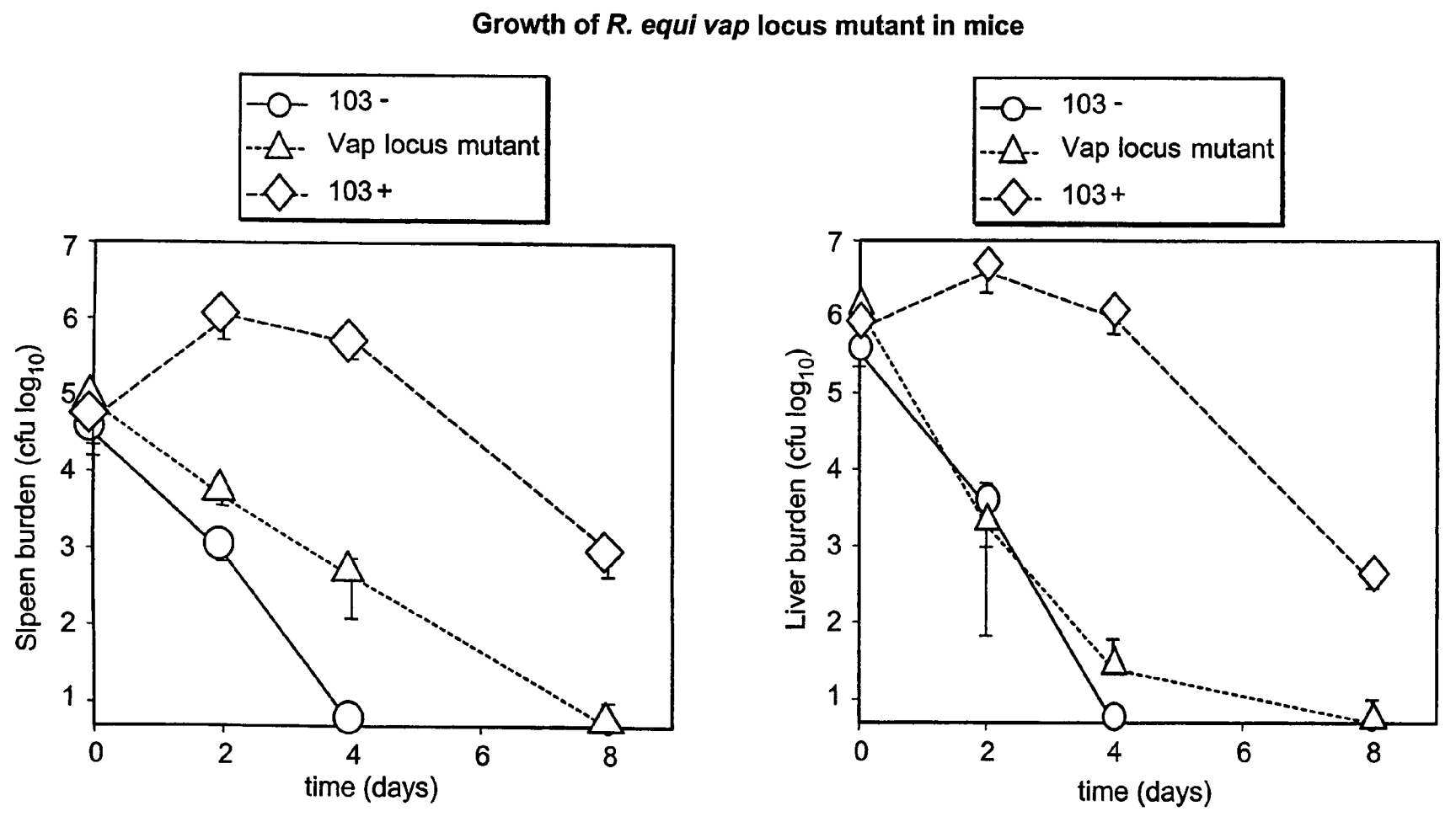

FIGS. 20A and 20B are a pair of graphs showing the growth of the *R. equi* vap locus mutant (▲) in mice over 8 days (y-axis) in spleen (FIG. 20A) and liver (FIG. 20B).

FIGS. 22A and 22B are a pair of graphs showing the clearance of the *R. equi* vap locus mutant (■) and complemented strains in mice over 8 days (y-axis) in spleen (FIG. 22A) and liver (FIG. 22B), versus controls (♦).

DETAILED DESCRIPTION

Figure 1:
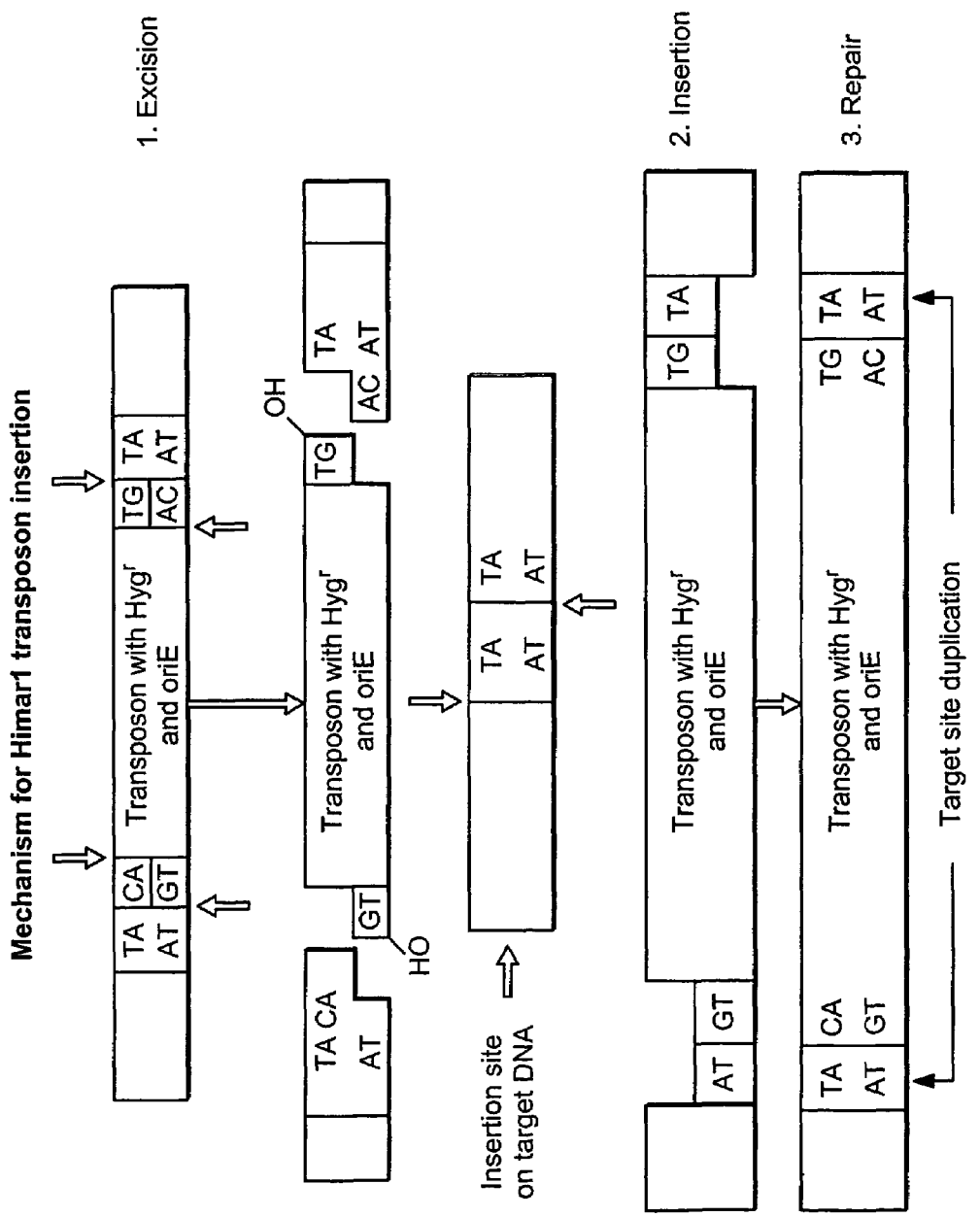
FIG. 1 is a diagram illustrating the mechanism for Himar1 transposon insertion.
Figure 2:
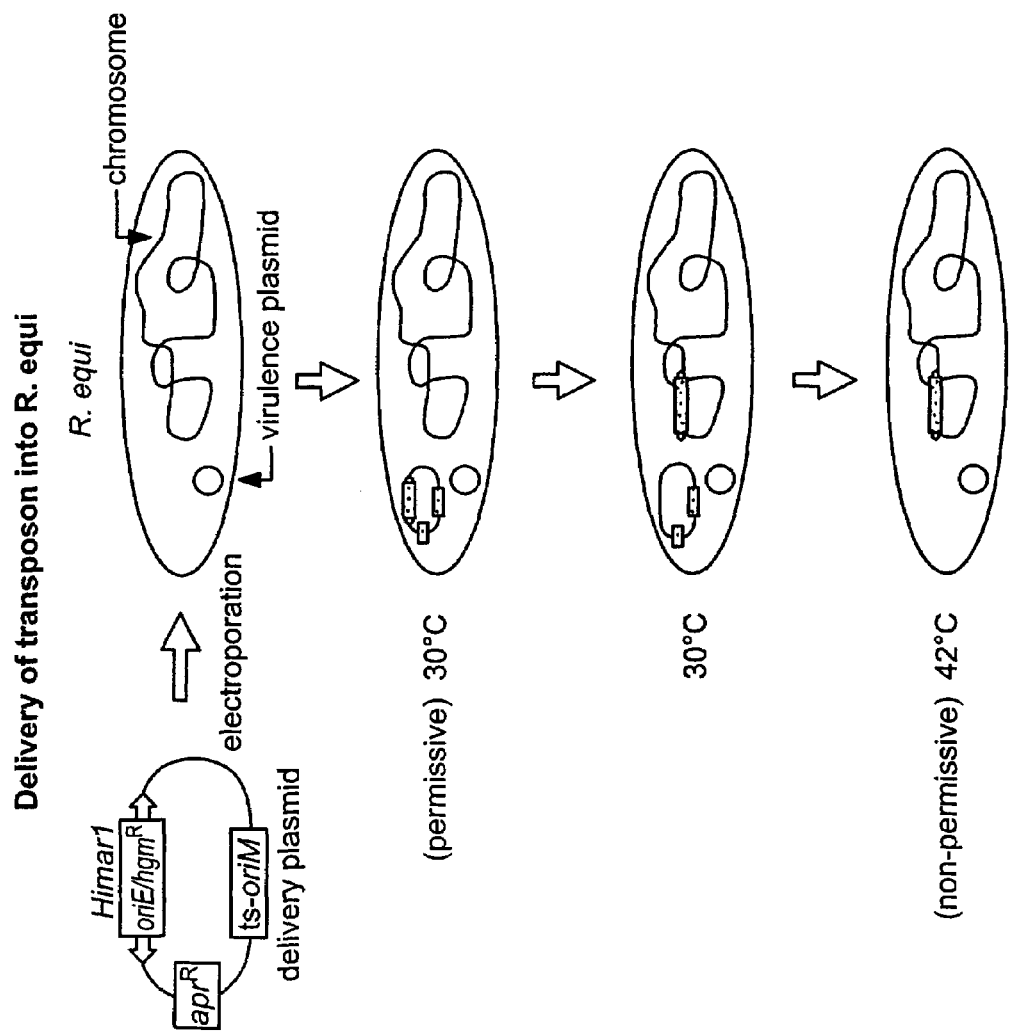
FIG. 2 is a diagram showing the delivery of the transposon into *R. equi*.
Figure 3:
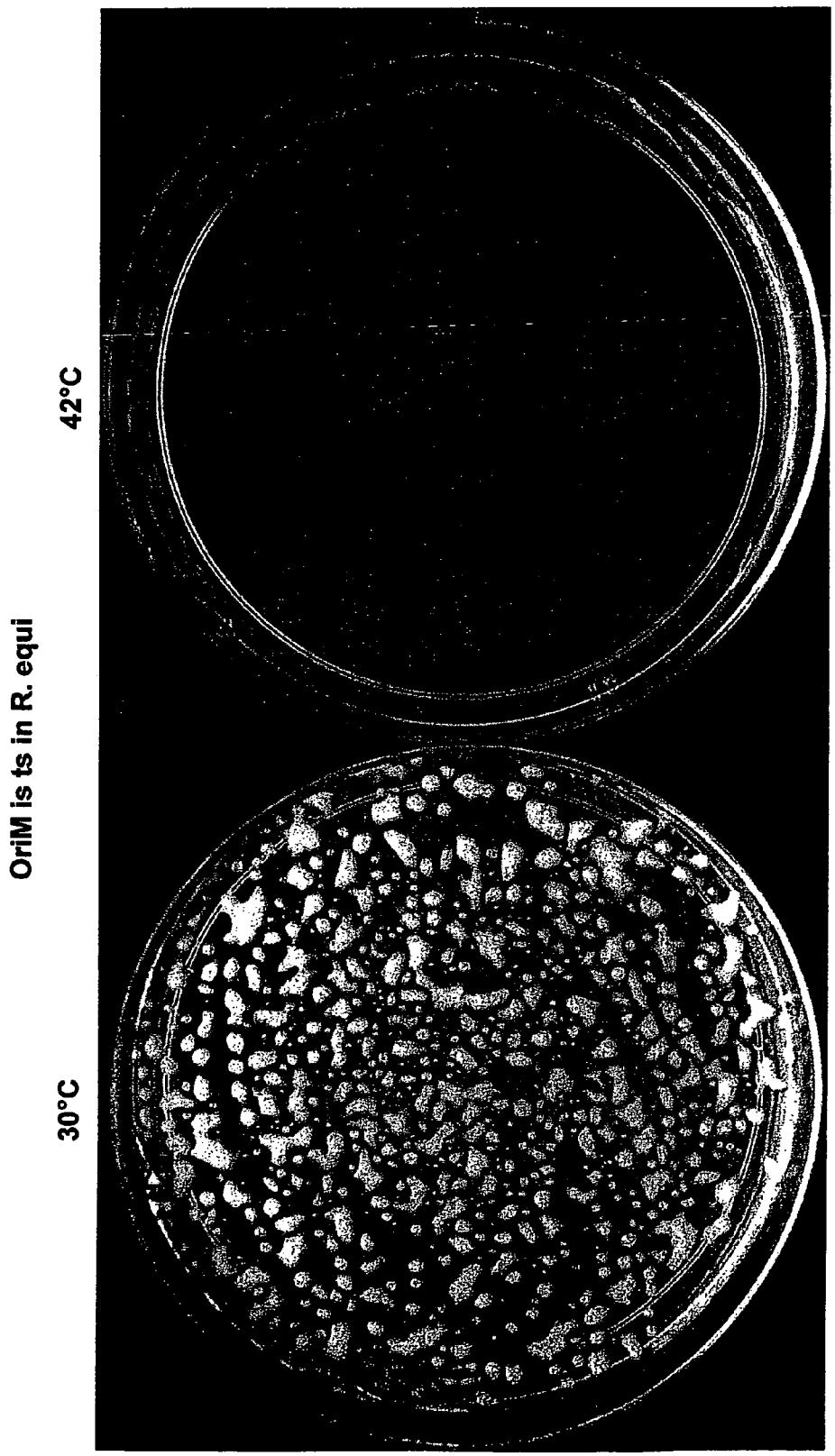
FIG. 3 is a photograph showing that OriM is temperature-sensitive in *R. equi*.
Figure 4:
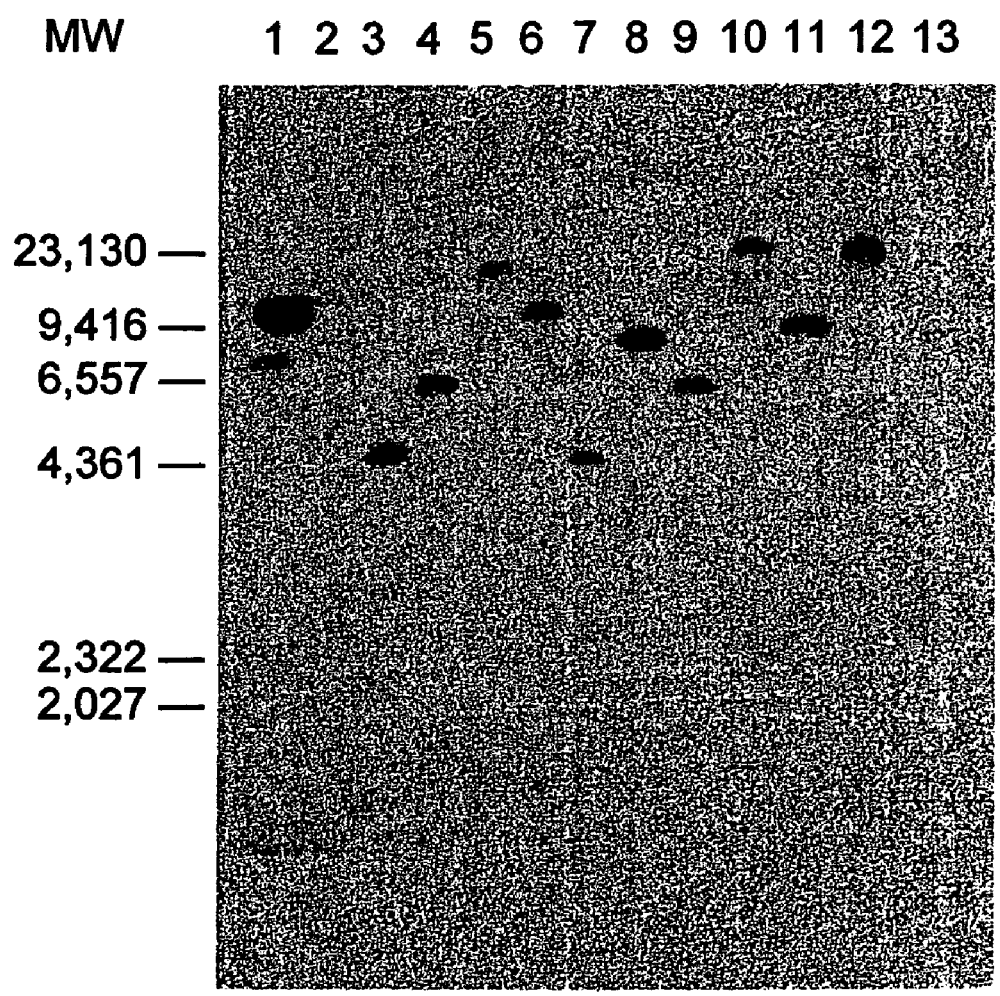
FIG. 4 is a Southern blot showing a number of randomly chosen *R. equi* transposon mutants.
Figure 6:
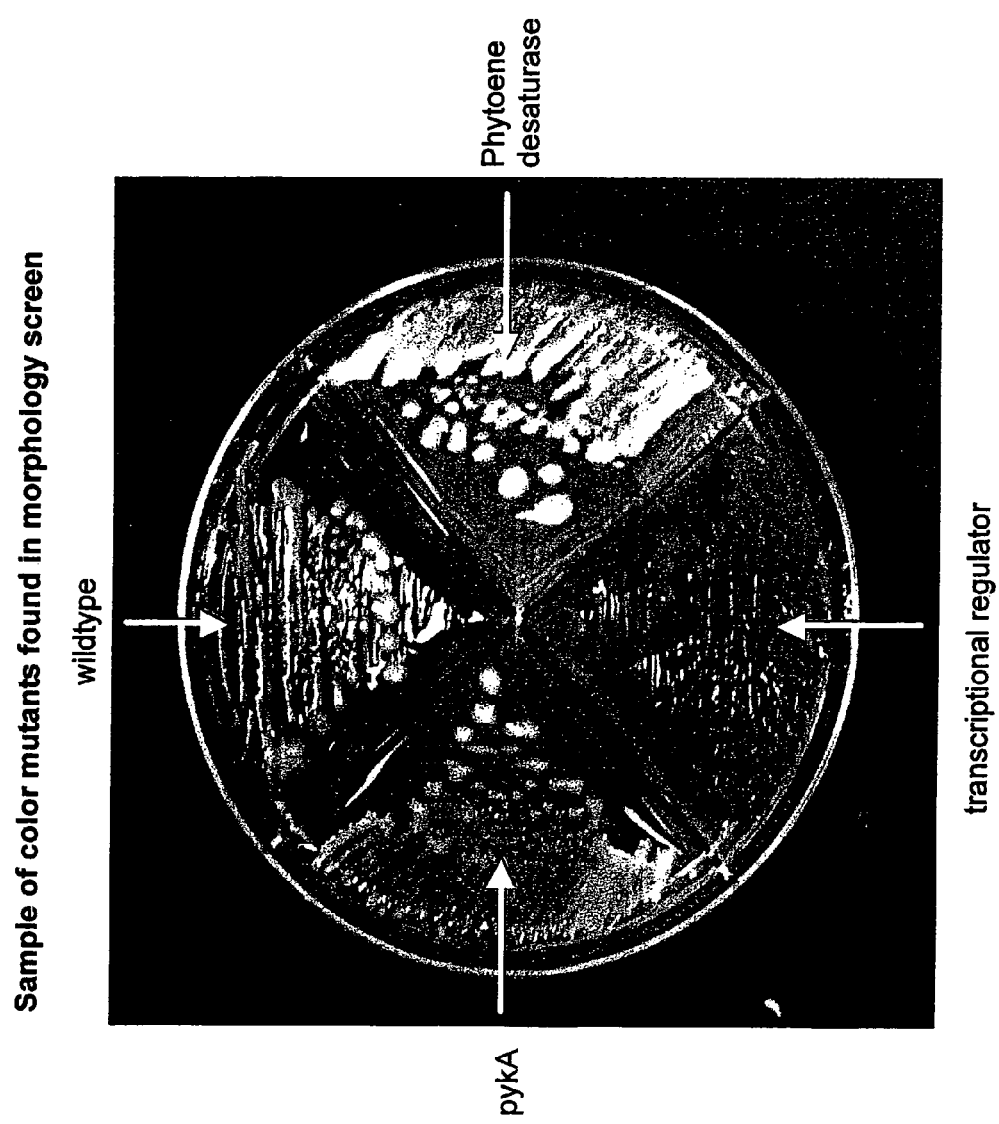
FIG. 6 is a photograph showing a sample of the color mutants found in the morphology screen.
Figure 7:
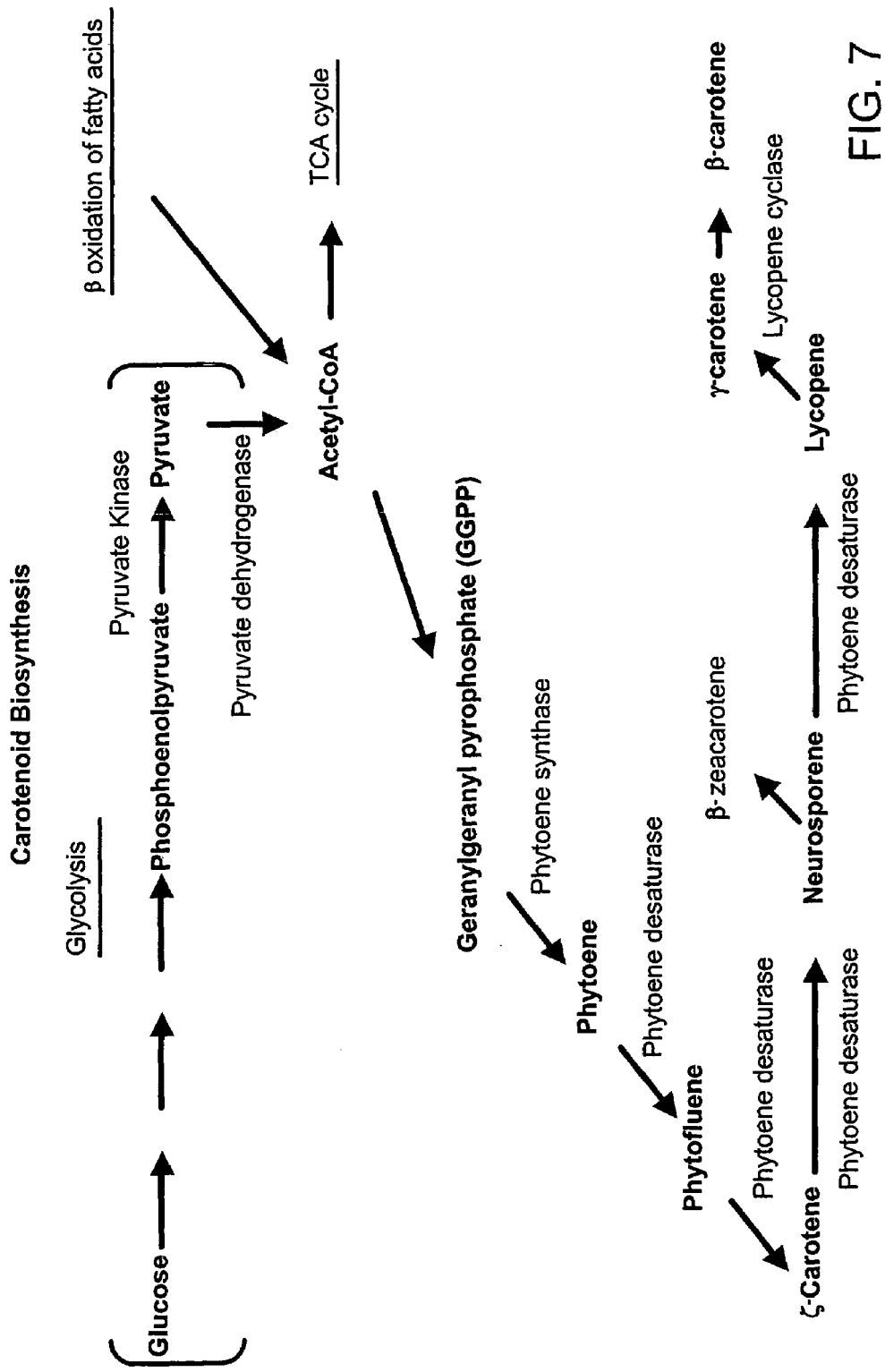
FIG. 7 is a diagram of the carotenoid biosynthesis pathway.
Figure 8:
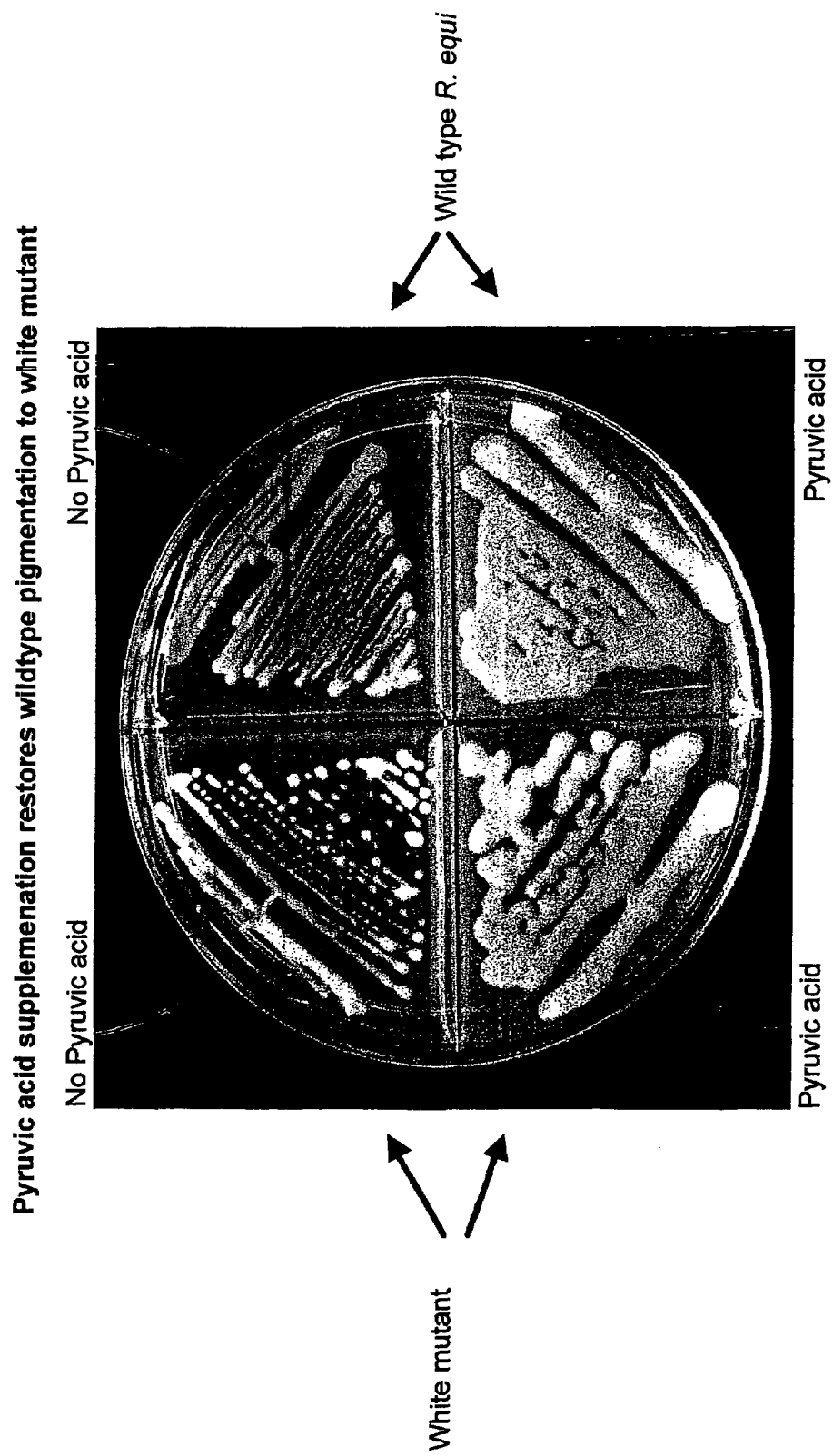
FIG. 8 is a photograph showing that pyruvic acid supplementation restores wildtype pigmentation to the white *R. equi* mutant.
Figure 9:
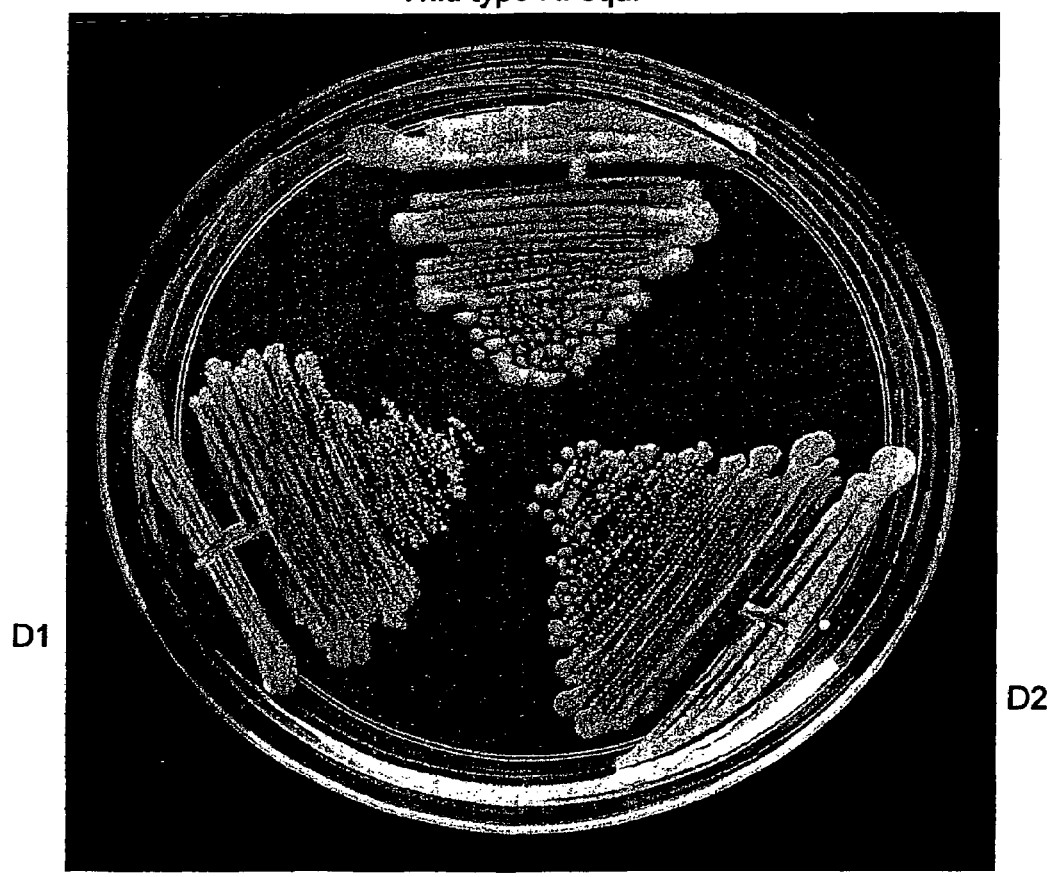
FIG. 9 is a photograph showing the different capsular phenotypes found in the morphology screen.
Figure 10:
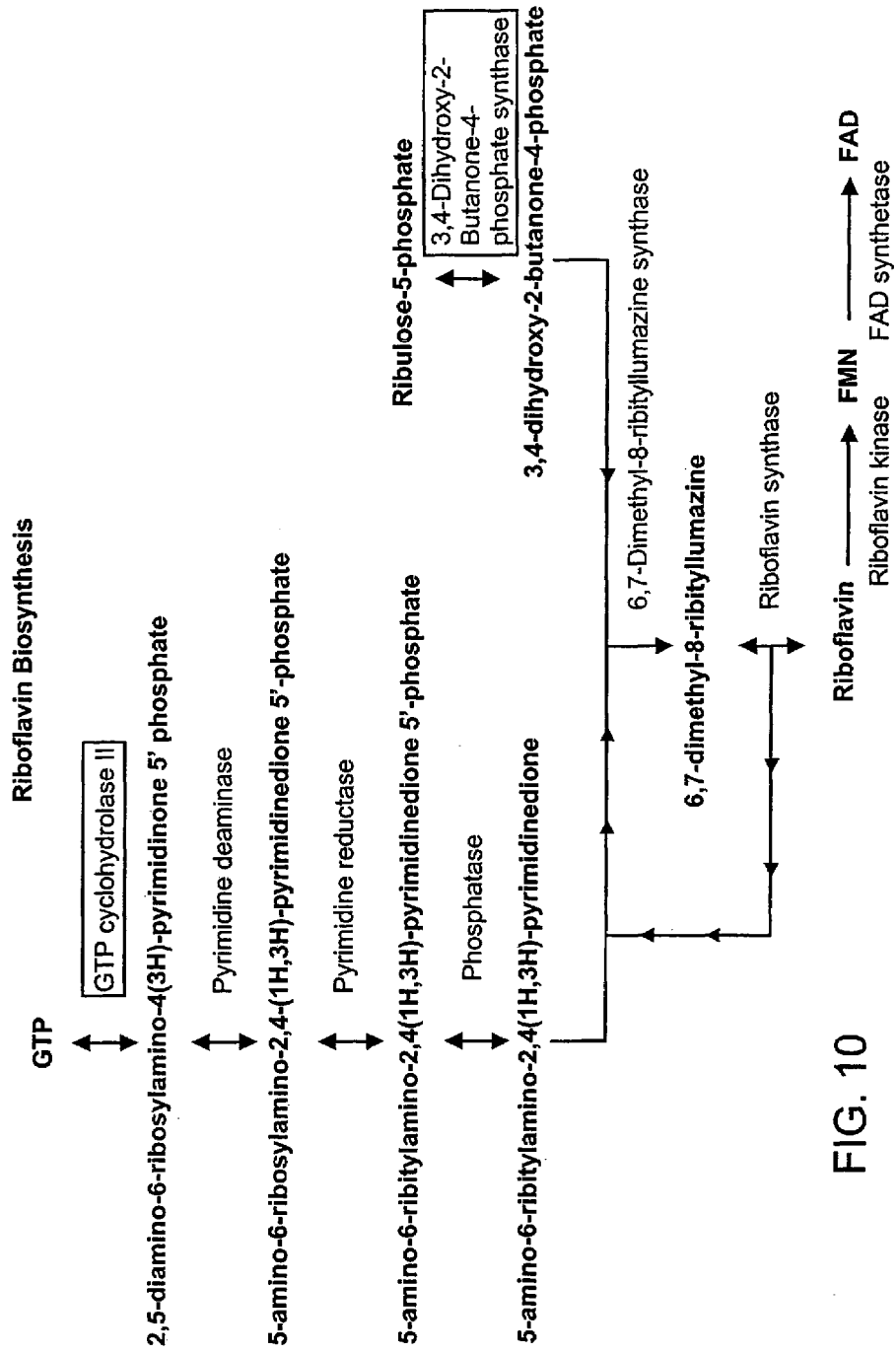
FIG. 10 is a diagram of the riboflavin biosynthesis pathway.
Figure 11:
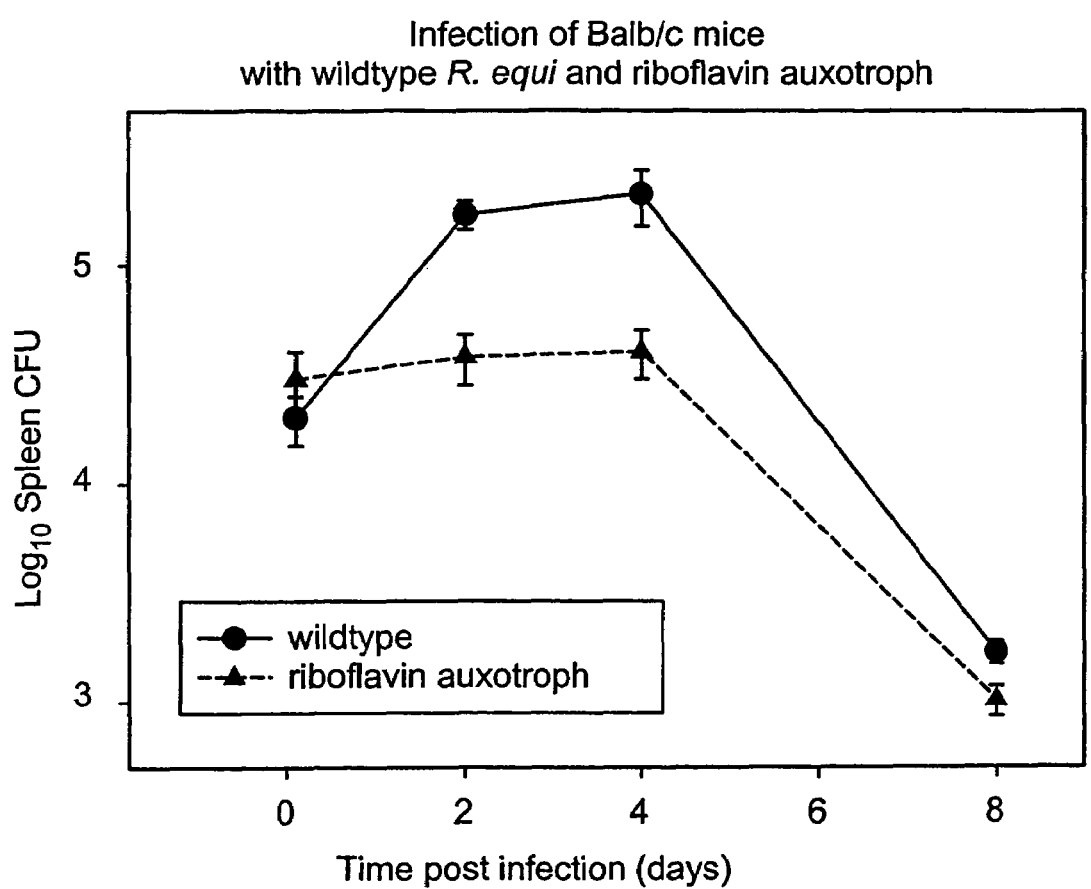
FIG. 11 is a graph showing the comparative clearance in mice of wildtype *R. equi* and the riboflavin auxotroph *R. equi* mutant.
Figure 12:
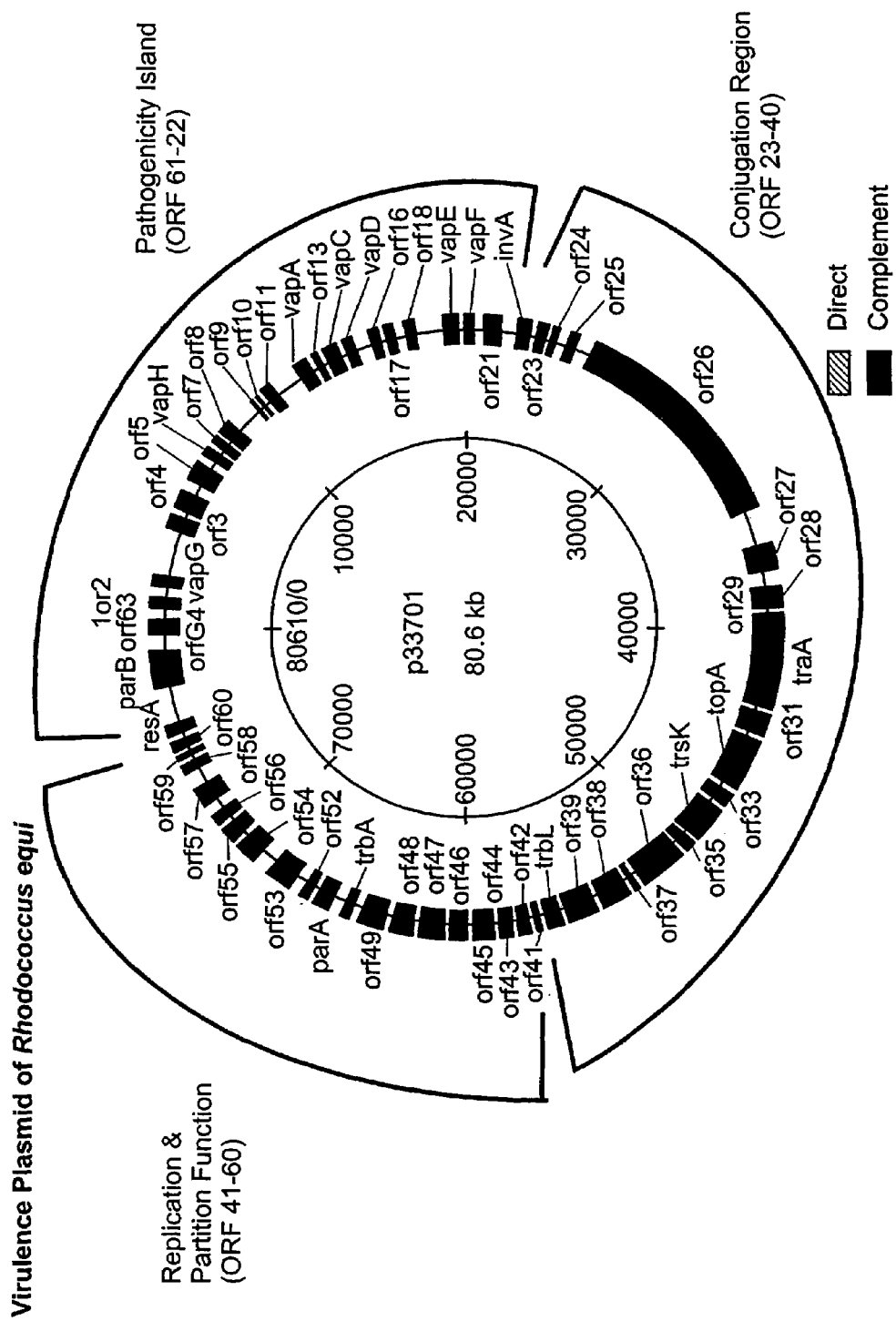
FIG. 12 is a diagram illustrating the virulence plasmid of *R. equi*.
Figure 13B:
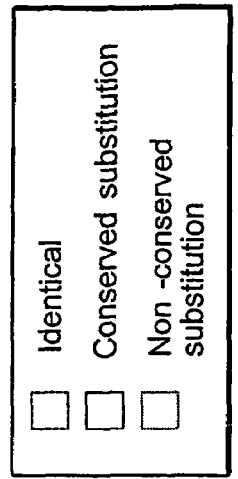
FIG. 13 is a sequence alignment of Vap proteins (SEQ ID Nos: 31-37).
Figure 14:
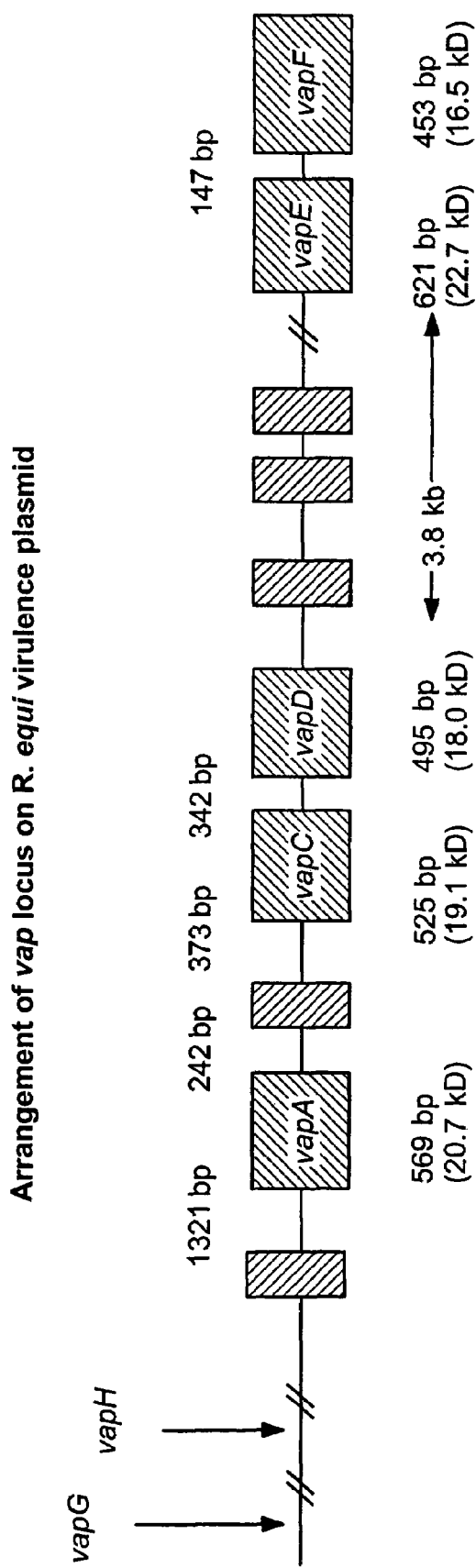
FIG. 14 is a diagram illustrating the arrangement of the vap locus on the *R. equi* virulence plasmid.
Figure 15:
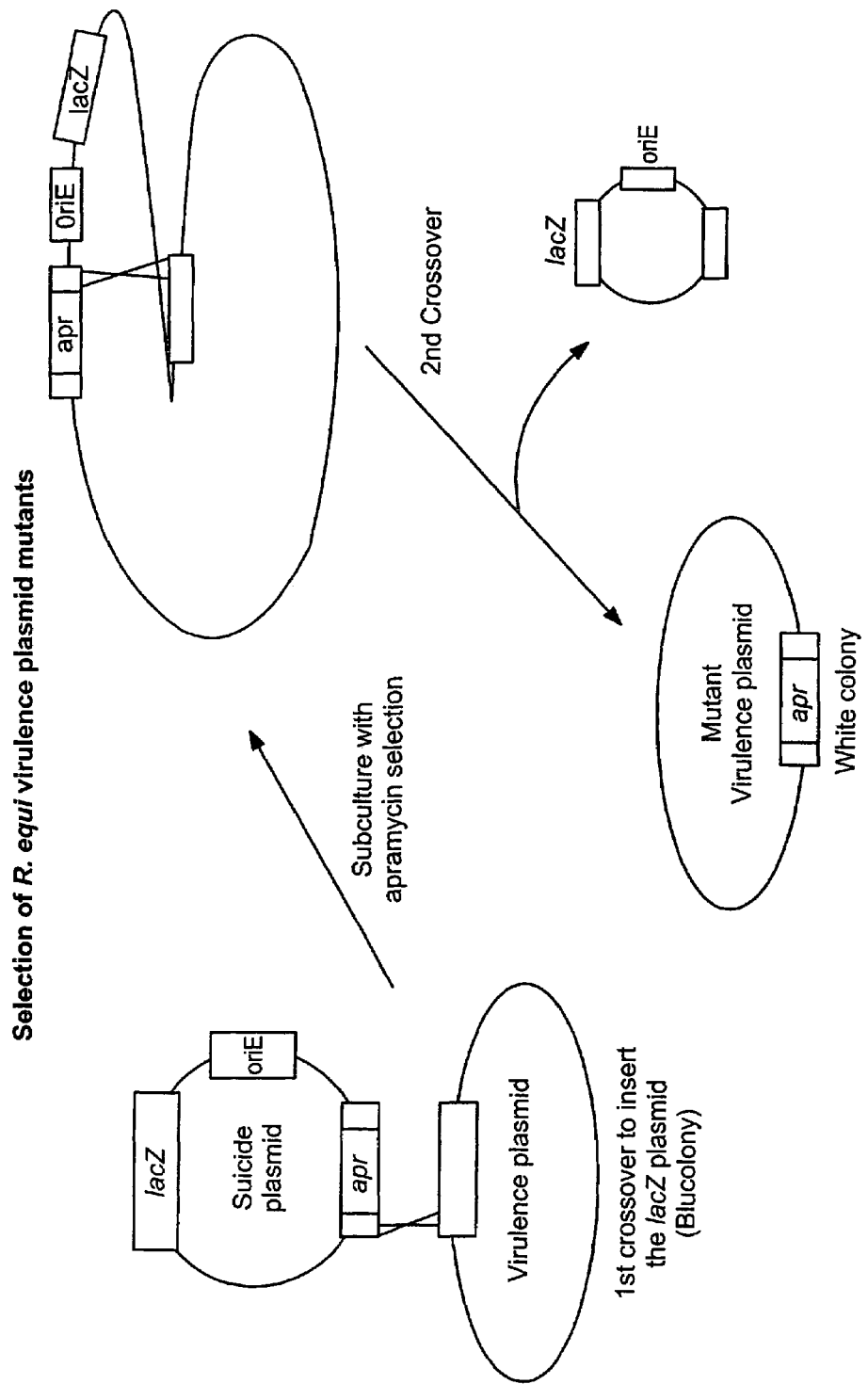
FIG. 15 is a diagram illustrating the selection of *R. equi* virulence plasmid mutants.
Figure 16:
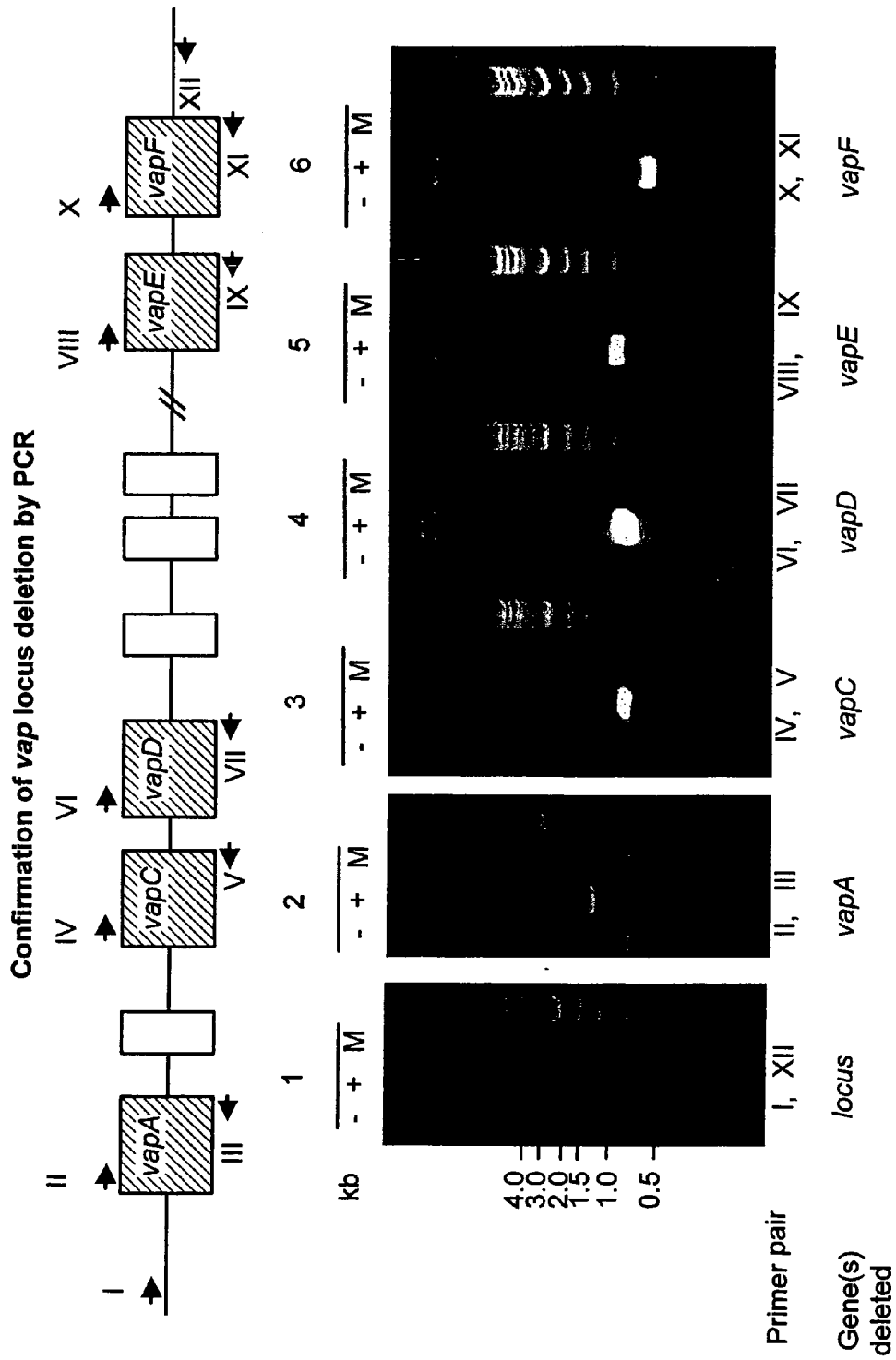
FIG. 16 shows the confirmation of the deletion of the vap locus.
Figure 17:
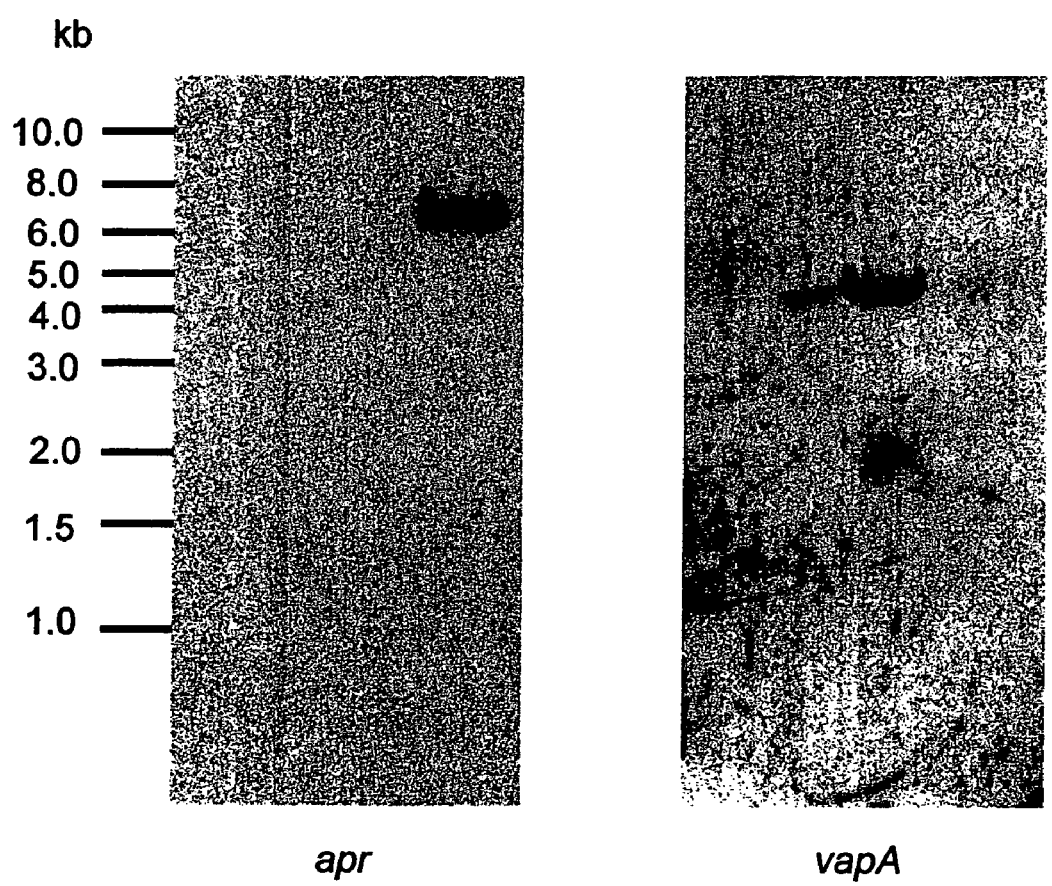
FIG. 17 is a Southern blot showing the *R. equi* vap locus mutant, relative to the apr mutant.
Figure 18A:
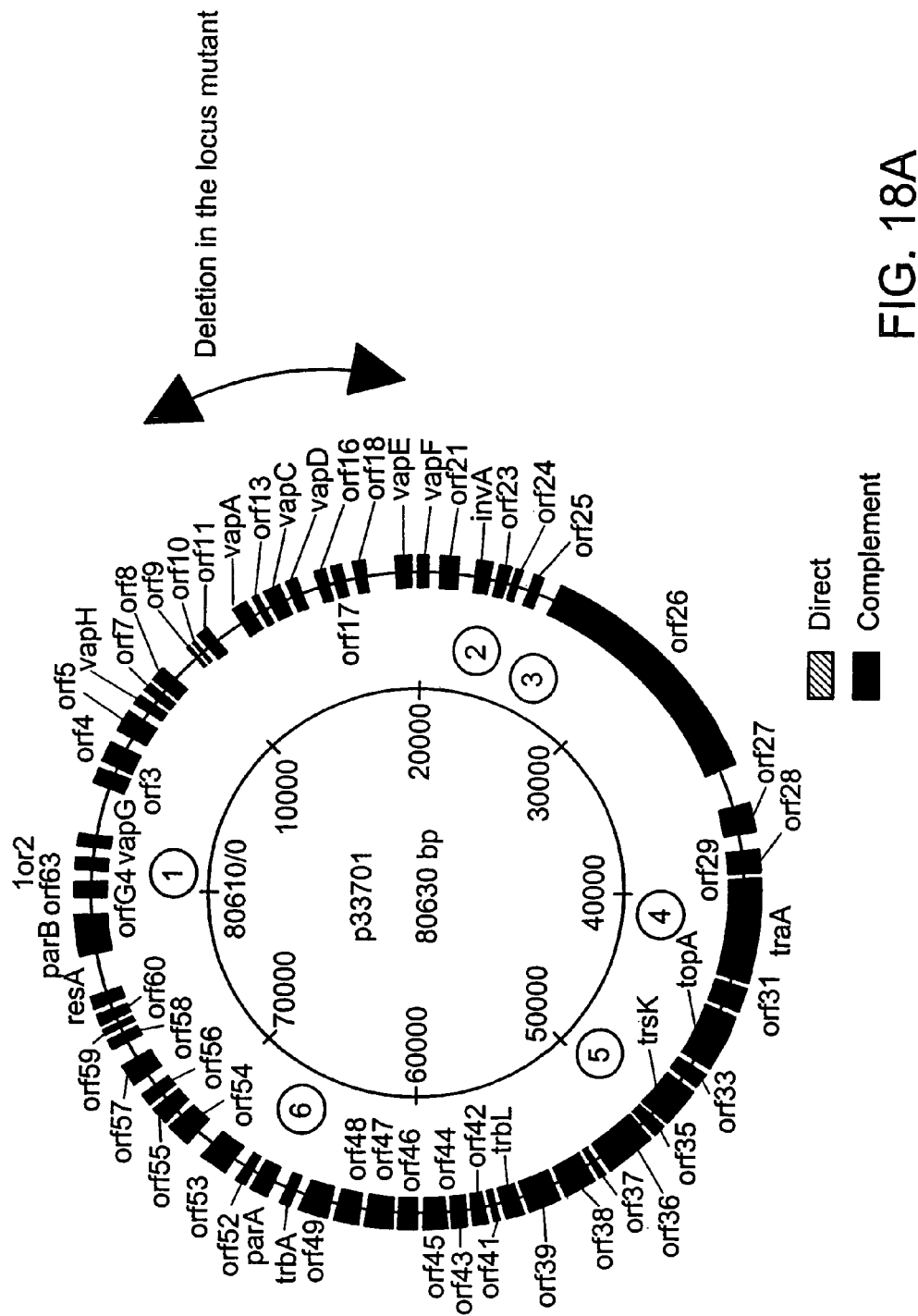
FIGS. 18A and 18B are, respectively, a diagram illustrating the location of the deletion on the vap mutant, and a gel showing confirmation of the integrity of the virulence plasmid in the mutants.
Figure 18B:
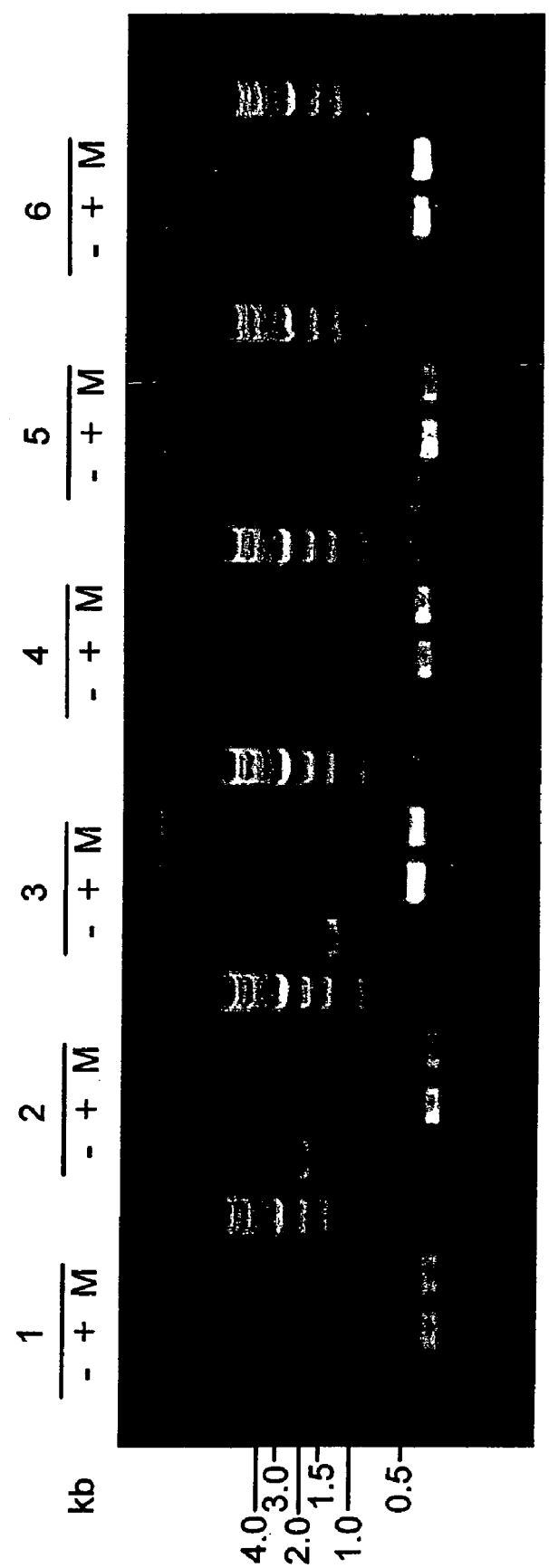
Figure 19:
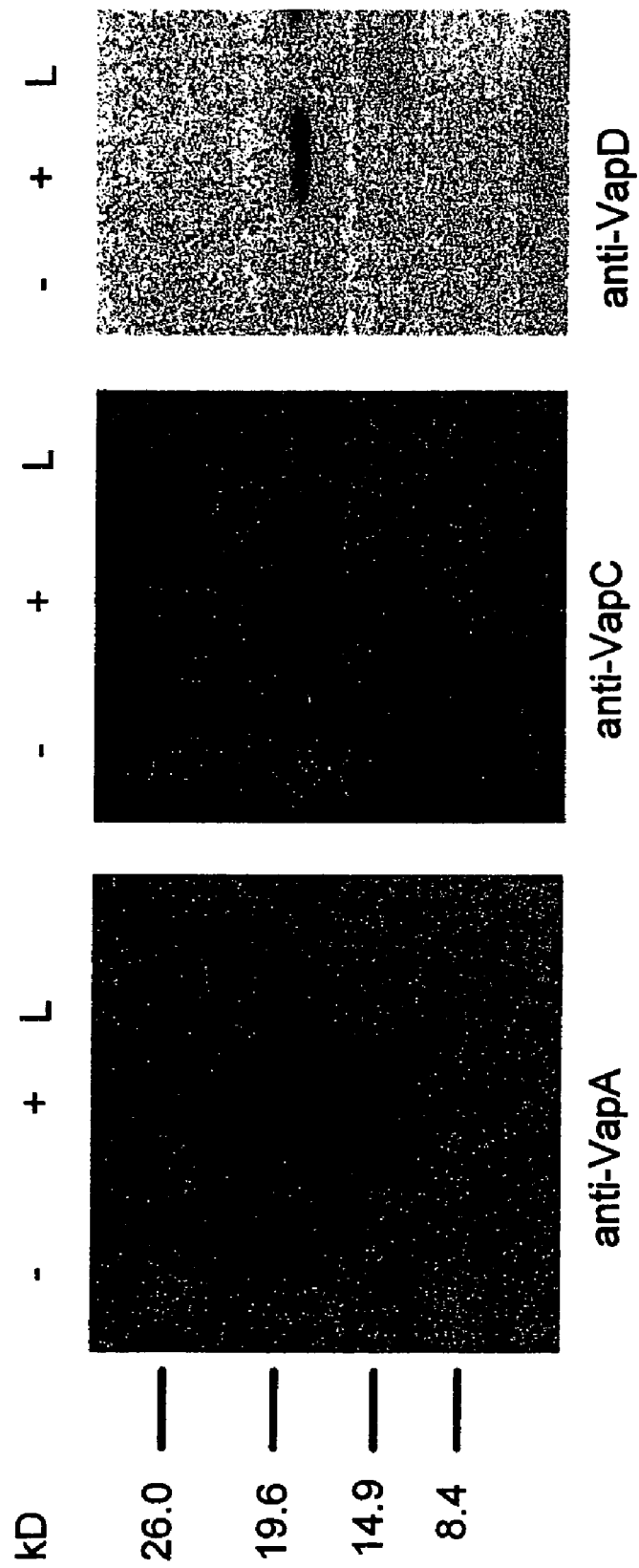
FIG. 19 is a western blot analysis of the *R. equi* cap locus mutant.
Figure 21:
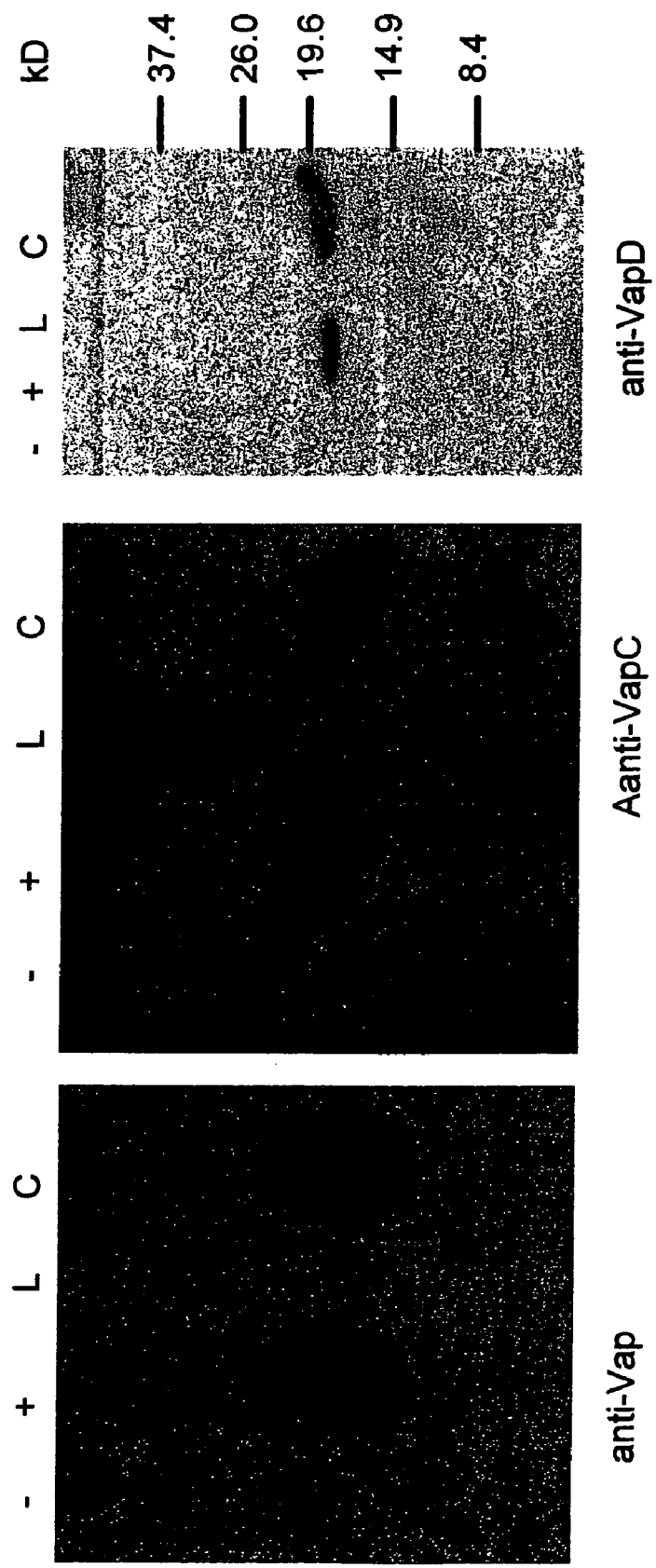
FIG. 21 is a set of three western blots of the complemented *R. equi* vap mutant.
Figure 23:
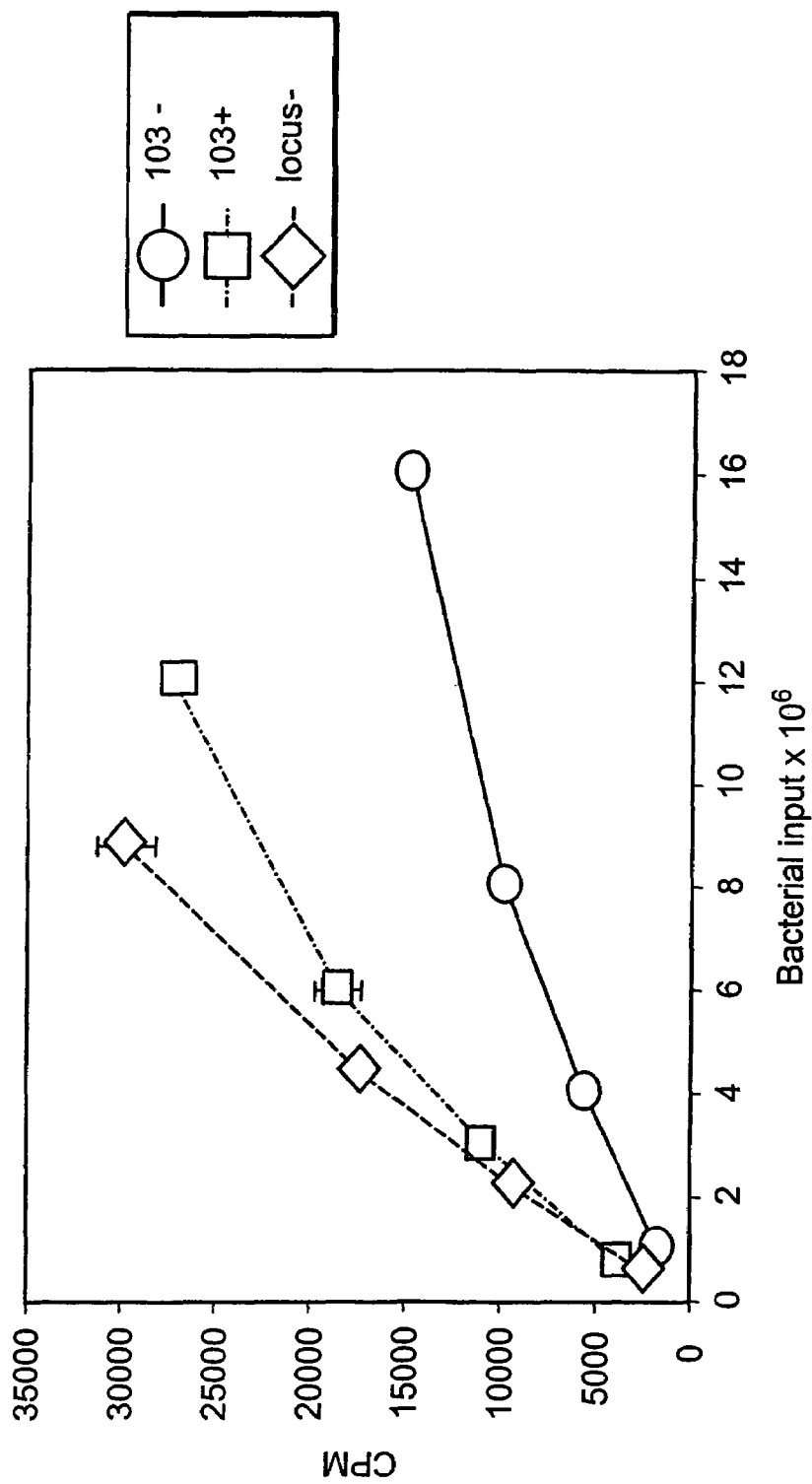
FIG. 23 is a graph showing the binding of $^3$H labeled *R. equi* to murine bone marrow-derived macrophages.
Figure 24:
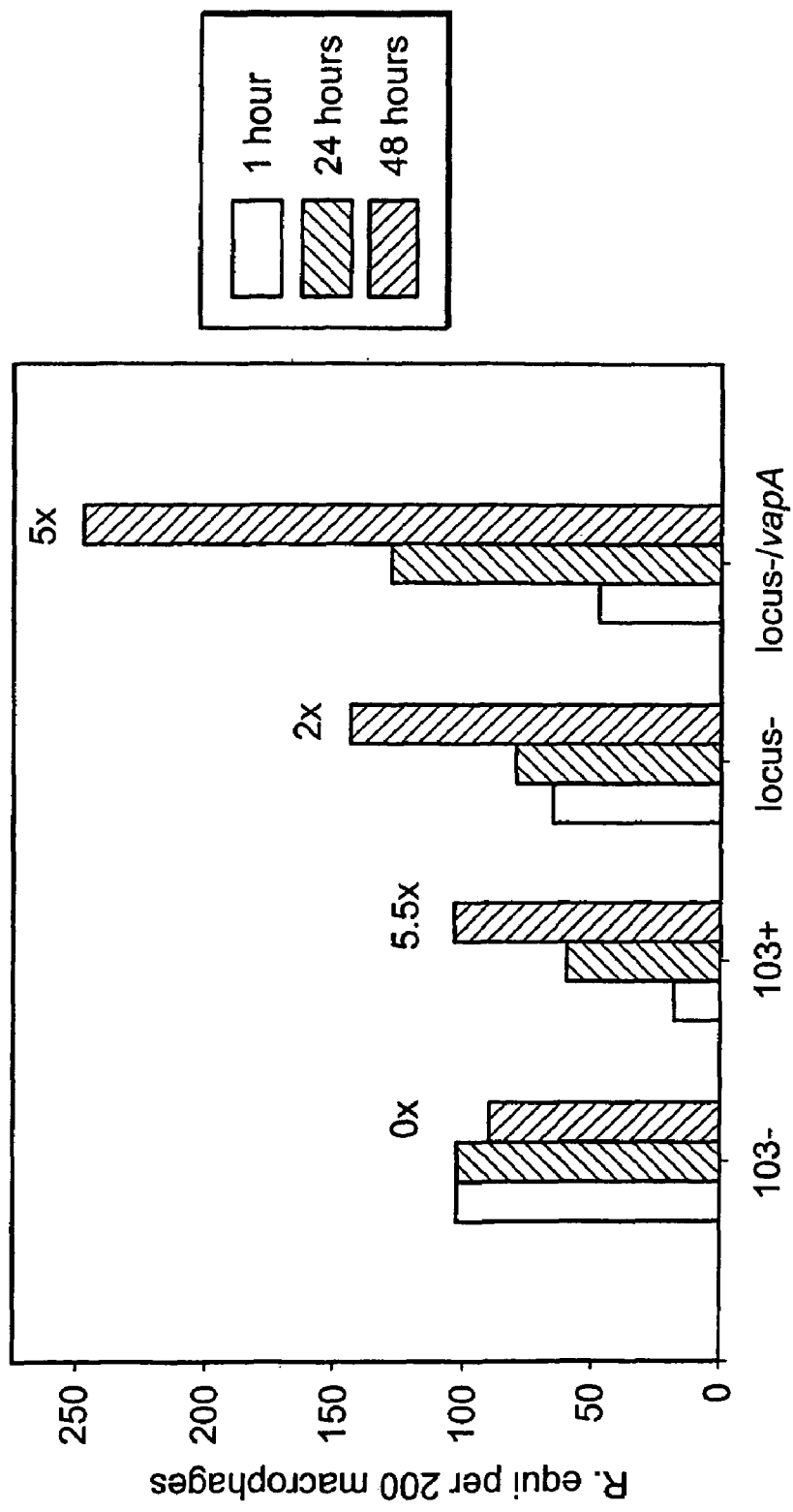
FIG. 24 is a bar chart showing the intracellular growth of *R. equi* strains in mouse bone marrow-derived macrophages at (bars from left to right for each strain) 1 hour, 24 hours and 48 hours.
Figure 25:
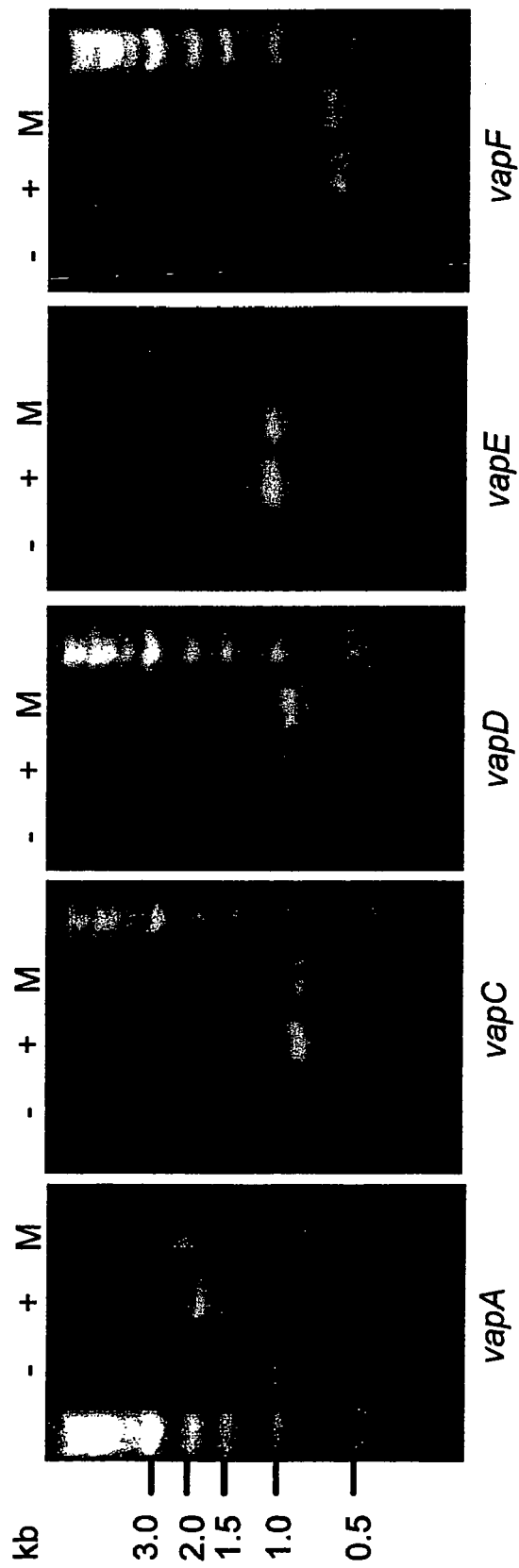
FIG. 25 is a set of four gels showing confirmation of the *R. equi* vapA mutant.
Figure 26:
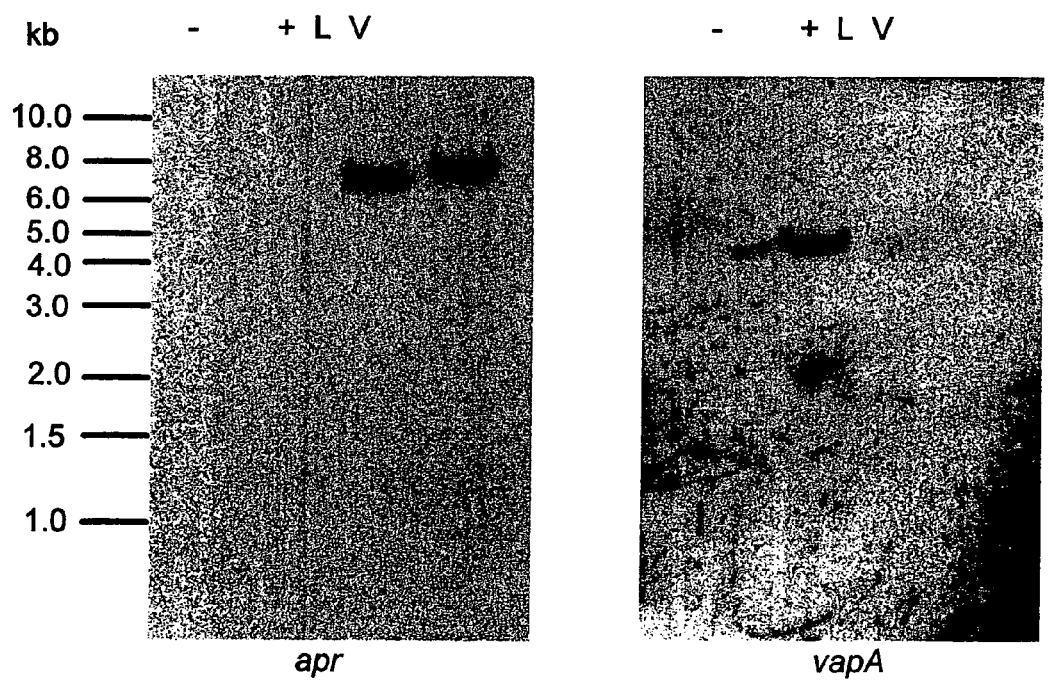
FIG. 26 is a Southern blot analysis of *R. equi* vap locus and vapA mutants.
Figure 27:
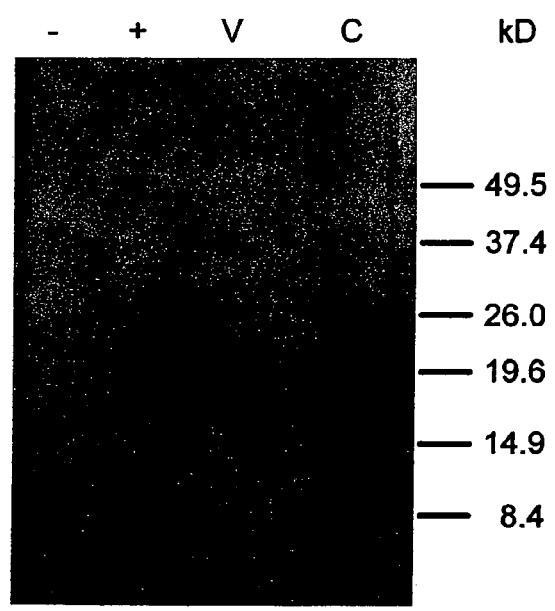
FIG. 27 is a western blot analysis showing the complementation of the *R. equi* vapA mutant.
Figure 28B:
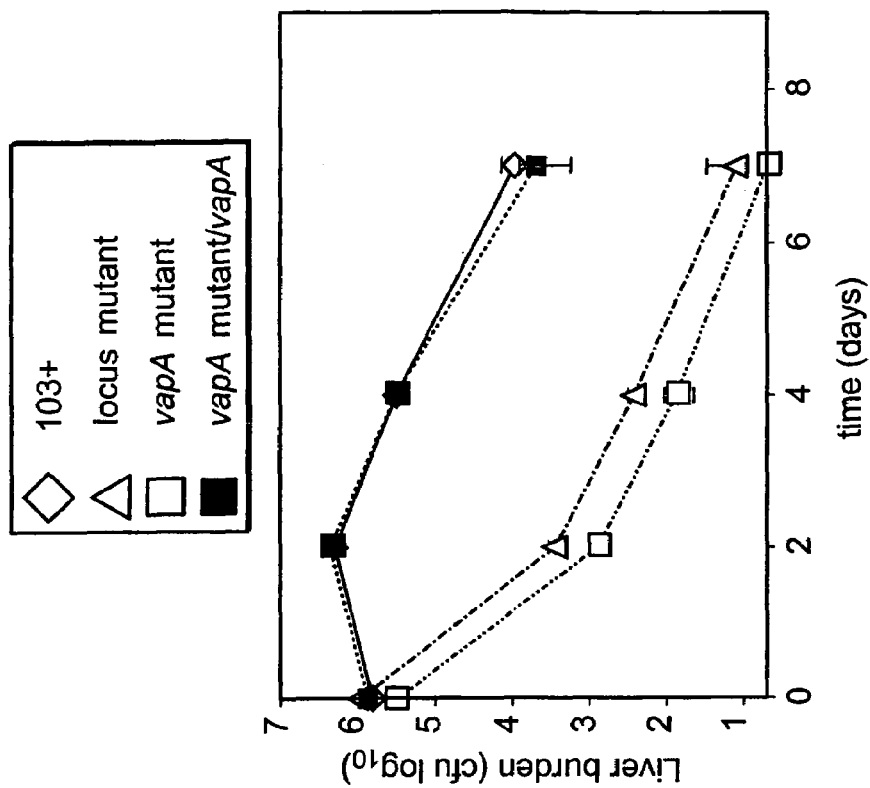
FIGS. 28A and 28B are a pair of graphs showing the clearance of the *R. equi* vapA mutant 8 days (y-axis) for the locus mutant (▲), the vapA mutant (□) and the vapA mutant/vapA (■) in spleen (FIG. 28A) and liver (FIG. 28B), versus controls (♦).
Figure 28A:
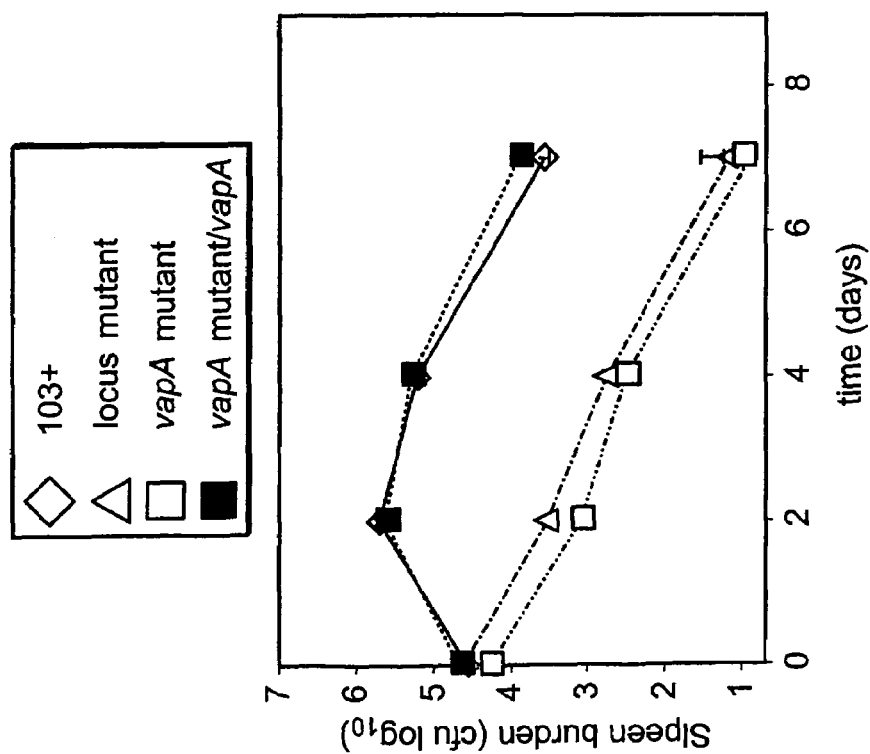

*Rhodococcus equi* is an intracellular opportunistic pathogen of immunocompromised people and a major cause of pneumonia in young horses. Study of the basic biology of this organism has been hampered by the lack of a developed genetic system and the tools with which to create mutants. Toward that end, we have developed an efficient transposon mutagenesis system that makes use of a Himar1 minitransposon delivered by a conditionally replicating plasmid. Transposition in *R. equi* is random, needs no apparent consensus sequence beyond the required TA dinucleotide and yields a diverse range of insertional mutations. We were readily able to screen for and identify pigmentation, capsular and auxotrophic mutants. An auxotroph so identified contained a trarisposon insertion in the gene encoding a putative duel functioning GTP cyclohydrolase/3,4-dihydroxy-2-butanone-4-phosphate synthase (DHBP synthase), an enzyme essential for riboflavin biosynthesis. In experimental murine infection studies, contrary to wildtype *R. equi*, the riboflavin-requiring mutant was unable to replicate in vivo. This methodology enables the characterization of *R. equi* virulence mechanisms, as well as allow the isolation of live-attenuated mutants for vaccine development.

Virulent strains of *Rhodococcus equi* carry an 80.6 kb virulence plasmid and express a highly immunogenic protein of 15-17 kDa which is designated as VapA (for virulence associated protein A). VapA has been implicated in the virulence of *R. equi* but thus far, there has been no evidence to prove this premise. Sequencing of the virulence plasmid recently revealed the presence of a total of 7 vap genes including vapA within its pathogenicity island. The proteins encoded by these genes exhibit significant homology in their C-terminal halves. It is known that VapC, VapD and VapE are secreted into the culture medium whereas VapA is located on the surface of the bacteria. In this study we describe construction of an *R. equi* mutant deleted for an 8 kb DNA region spanning the 5 vap genes namely vapA, vapC, vapD, vapE and vapF. This mutant was unable to multiply in mice and was rapidly cleared in comparison to the wild type strain suggesting an attenuation of virulent *R. equi* in the absence of these vap genes. We complemented the mutant strain with each of the missing vap genes individually and tested the resultant strains in mice for restoration of the virulence phenotype. The mutant strain that was complemented with vapA was restored to full virulence, whereas the other 4 vap complemented strains were not. Furthermore, the mutant strain exhibited an intracellular growth defect although its binding to bone marrow derived murine macrophages was normal. Our observations provide the first proof of a role for VapA in the virulence of *R. equi*.

Transposon-based mutagenesis is a powerful technique that is virtually essential for conducting thorough investigations of bacterial virulence, and its use has lead to the identification of virulence determinates in a variety of bacterial systems [Gaillard, 1986 #547] [Gulig, 1988 #548] [Mills, 1995 #549]. This technique involves using a mobile DNA element to randomly disrupt host genes through transpositional insertion. Hence, our objective was to develop a transposon-based mutagenesis system for use in *R. equi* so that we could begin to decipher the molecular requirements of disease development. Moreover, the approach provides a means to create attenuated bacterial strains with the potential for use as live-attenuated vaccines and thus, may yield a path to disease prevention.

Naturally occurring transposable elements have been discovered in both Gram-positive and Gram-negative bacteria (Rowland S J and Dyke K. G., 1990, Mol Micro 4:961) and subsequently engineered to construct insertion mutation systems for several bacterial species using both in vivo and in vitro delivery methods (Craig, N L, 1997, Annu Rev Biochem; Griffin T, Grindley, N. D. F. Nuc. Acids Res., 1999 27:3859). However, transposon systems frequently possess shortcomings, one of the most common limitations being host range restrictions and site-specific integration, such as is observed with Tn10 integration in *Mycobacteria* spp. (Bardarov et al, PNAS, 94:10961, 1997). We chose to develop a mutagenesis system that employed the transposable element Himar1, a member of the mariner family of transposons, originally isolated from the horn fly *Haematobia irritans*. A particular advantage of this element is its minimal site specificity and apparent lack of requirement for host accessory proteins (Lampe D. J. Churchill and Robertson H. M. 1996 EMBO J. 15:5470). Apart from the required TA dinucleotide, there are evidently no other requisite sequence determinants for insertion (Lampe d. J, Grant and Robertson H. M., Genetics 1998, 149:179) In addition, the Himar1 element has been demonstrated to transpose randomly in both eukaryotic cells and bacteria including *E. coli* and the closely related *Mycobacteria* spp. (Plasterk R, Ivics, Z Trends in Genetics, 1999, 15:326, Rubin 1999). A Himar1-based transposon would likewise insert randomly within the genome of *R. equi*, and as disclosed herein, we found this to be the case. Using a conditionally replicating plasmid to delivery the mini-transposon, we have efficiently generated a random insertional mutant library in a virulent strain of *R. equi*. We have confirmed a lack of insertion site specificity and a minimum of target bias. Importantly, screening of the library easily identified several morphology mutants (color and capsular changes). In addition, we isolated a riboflavin auxotroph in which the transposon had inserted within the gene encoding the bifunctional enzyme GTP cyclohydrolase II/3,4-dihydroxy-2-butanone-4-phosphate synthase, a member of the riboflavin biosynthesis pathway. We have determined that this riboflavin auxotroph is attenuated in an in vivo murine model system of *R. equi* infection. In addition, this mutagenesis system will be extremely useful in deciphering the pathogenesis of *R. equi* infection, the study of which has been hampered by a paucity of molecular tools with which conduct a thorough genetic analysis.

Analysis of *R. equi* pathogenesis has been hindered by the lack of a genetic system and a means to readily create mutants. For that reason, we set out to develop a mutagenesis protocol for *R. equi* founded on transposon-mediated gene disruption. During the course of this work, another laboratory reported using a commercially available kit to achieve transposome-mediated gene inactivation in *R. equi* (Mangan and Meijer). We had attempted a similar approach, but our results were less successful and therefore, we decided to develop our own system based on the Himar1 transposable element.

Himar1 is a member of the mariner family of short-inverted, terminal repeat-type mobile DNA elements that transpose via a simple cut-and-paste mechanism (Plasterk R and Z. Ivics, 1999, Trends in Genetics). mariner elements are part of a large superfamily of transposons, the Tc1/mariner family, whose homologs can be found in nematodes, insects, fish, humans, fungi and plants. Family members are similar in structure; and in the native context, terminal repeats frame the transposase, the lone transposon gene, and serve as binding sites for this enzyme. Members of the mariner family have among the simplest and shortest terminal repeat structure (Plasterk); for example, the transposon used in this study is flanked by a 29 bp repeat sequence. Binding of the transposase to the terminal repeats results in a staggered double strand DNA break at either side of the transposon causing excision of an element whose termini have a single-strand, 2 bp overhang with a reactive 3' hydroxyl group. Insertion involves another staggered double strand DNA break that occurs at the TA dinucleotide of the target site. Following integration, repair of the single strand gap leads to duplication of the TA target site and a produces a frameshift. Integration reportedly occurs almost exclusively at a TA dinucleotide (Plasterk), a finding we documented in 100% of the *R. equi* insertion mutants. As anticipated, we have confirmed a lack of target specificity, since no consensus sequence was identified beyond that of the TA integration site. Importantly, even in the GC rich genome of *R. equi*, insertion was random and a variety of unique insertions were obtained; specifically 87 out of 100 clones examined contained a distinct insertion. We observed a minimum of target bias consistent with what has been reported for mariner transposition in other systems (Rubin, Lampe D and Robertson H 1998, Genetics 149:179). It has been shown that DNA sequence structure adjacent to the TA dinucleotide can influence insertion frequency such that a preference toward insertion into bendable DNA sequences has been found (Brukner I et al., 1995 EMBO 14:1812), presumably because the accessibility of the regional TA is thereby increased (Brukner; Lampe and Robertson, Genetics). Upon analysis of a hundred randomly chosen insertion mutants we noted two regions of sequence that were targeted more than once. Specifically the ORF of a putative penicillin binding protein was identified three times, although the insertion sites differed, and a ribosomal RNA gene was a target twice, but again each insertion was distinct. Although the particular target TA was unique in the aforementioned clones, we question whether the molecular structure of those regions of the genome might be somehow more conducive to transposon insertion.

*R. equi* is a member of the nocardioform actinomycete genre and has much in common with another actinomycete, *M. tuberculosis* (Hondalus and Mosser). Physical commonalties include GC rich (>65%) DNA, and a cell wall containing an abundance of arabinogalactan and mycolic acids. Both bacterial species parasitize alveolar macrophages, disrupt normal endocytic trafficking, replicate intracellularly, and cause a granulomatous pneumonia (Hondalus and Mosser). Given the similarities of the two organisms and the relative lack of genetic tools available for analyzing *R. equi*, we reasoned that we should be able to make use of reagents used in the study of *mycobacteria* spp. In fact, we had previously determined that the oriM derived from the *M fortuitum* pAL500 plasmid could stably maintain an episomal *E. coli-Mycobacterium* shuttle vector in *R. equi* (Giguere and Hondalus). Pelicic and colleagues had created a temperature sensitive version (ts) of the oriM which could promote plasmid replication in *mycobacteria* grown at 30° C. but which ceased to function at 39° C. We tested this ts-oriM in *R. equi* and determined that it was similarly temperature sensitive. In *R. equi* transformed with our transposon delivery plasmid containing the ts oriM, growth at the non-permissive temperature (42° C.) resulted in a 5000-fold reduction in the number of colonies as compared to that obtained at the permissive temperature (30° C.), a reduction level similar to that observed in *mycobacteria* (Pelicic V PNAS 1995). After testing different temperatures, we ultimately chose 42° C. as the non-permissive temperature because fewer colonies escaped the selection at this temperature and because the bacteria tolerated growth at this temperature. We concluded that it was feasible to use a conditionally replicating plasmid as a means to deliver the Himar1 transposon to *R. equi*, as had been done in *M. smegmatis* (Rubin). We note that a limitation of this delivery method is the potential for the generation of sibling mutants. Insertions occurring early in the permissive outgrowth period can be over-represented following re-plating and incubation at the non-permissive temperature. To correct for this, it may be necessary to screen additional clones in order to identify a particular phenotype. Nonetheless, we were successful in performing several mutant screens.

As a demonstration of the potential utility of the mutagenesis, we screened for and readily obtained *R. equi* clones with altered pigmentation. *R. equi*, like many species of bacteria, fungi and plants, produce tetraterpenoid pigments known as carotenoids which are derived from the general isoprenoid biosynthesis pathway (ref one of the text books). These yellow, orange and red pigments provide protection against photooxidative damage induced by both visible and UV light as well as oxygen radicals (Armstrong PNAS; TuvesonR et al 1988 J.Bact 170:4675). In plants and photosynthetic bacteria, they serve a light capturing function for photosynthesis (Armstrong PNAS; Kuhlbrandt W. et al Nature 1994 367:614). A $C_{40}$ hydrocarbon backbone is common to all carotenes and is generated by the condensation of two molecules of geranylgeranyl pyrophosphate (GGPP) to create the colorless intermediate phytoene in the first reaction specific to the carotenoid biosynthesis branch of the isoprenoid pathway (Armstrong review; Sandmann F, 1994 FEBS). Phytoene then undergoes a series of desaturation reactions producing the sequential intermediates phytofluene, ζ-carotene, neurosporene and the maximally desaturated molecule lycopene. At the level of neurosporene or lycopene the carotenoid biosynthesis pathway diverges between organisms, giving rise to the approximately 600 unique cartenoids thus far identified (Staub, O. (1987) in: *Key to Carotenoids,* ed. Pfander, H., Birkhauser, Basel, p. 296). A single cyclization reaction at one end of lycopene yields γ-cartotene, the pigment found in abundance in *R. equi* (Ichiyama et al). In many other bacterial species including *Rhodococcus* (not *R. equi*), *Mycobacteria* spp., and *Erwinia* spp. both ends of lycopene are cyclized creating the pigment β-carotene (Ichiyama S et al 1989; Tsukamura M and Mizuno S. 1965 Med. Biol. 71:364, and Tuveson R., 1988, J. Bact 170:4675).

Transposon mutagenesis was used to discover the structural and regulatory genes of carotenoid biosynthesis in the bacterium *Myxococcus xanthus* (Fontes, M et al 1993 EMBO). As was the case in our study, the sequence of *M. xanthus* phytoene desaturase was identified in this way. Phytoene desaturase is the enzyme responsible for introducing double bonds in the $C_{40}$ hydrocarbon carotenoid backbone. The number of desaturation reactions varies amongst different organisms, but this single enzyme can carry out each dehydration step starting from phytoene and leading up to and including the branch intermediates neurosporene and lycopene (Sandmann F, 1994 FEBS). In one of the yellow-pigmented *R. equi* mutants, the transposon had inserted into an ORF with homology to phytoene desaturase and thus, the synthesis of γ-carotene was interrupted. Without performing high-pressure liquid chromatography (HPLC) we cannot definitively know what carotenoid(s) are present in this mutant. However, neurosporene is a yellow pigment and lycopene is red, and thus a mutant with a block before lycopene formation would be consistent with an alteration in phytoene desaturase activity. Mutants that fail to produce phytoene lack all carotenes and are colorless (Arrach N, PNAS 2001). A non-pigmented *R. equi* mutant we identified contained a transposon insertion into an ORF with high homology to the glycolytic enzyme pyruvate kinase. Pyruvate kinase mediates the transfer of phosphate from phosphoenolpyruvate to ADP yielding ATP and pyruvate a precursor of acetyl-coenzyme (acetyl-CoA). Alternatively, acetyl-CoA can be formed via β-oxidation of fatty acids. The first isoprenoid precursor is acetate, in the form of acetyl-CoA. Three molecules of acetyl-CoA are consumed in the general pathway reactions leading up to the GGPP intermediate. We reasoned that because of an inability to make sufficient amounts of pyruvate, the non-pigmented *R. equi* pyruvate kinase mutant might not be making adequate acetyl-CoA necessary to ultimately generate the pigment producing carotenoids. To help determine if the transposon disruption was the cause of the altered pigmentation, we grew the pyruvate kinase mutant in the presence of exogenous pyruvate. We found that pyruvate supplementation restored wildtype pigmentation to the mutant, a finding consistent with the idea that the transposon disruption caused the loss of pigmentation. Mutants that accumulate lycopene are more red in color (Arrach et al PNAS). Again, without proper analysis, it is impossible to know what carotenoids are present in the intensely orange-colored *R. equi* mutants we identified, but it may be that accumulated lycopene is responsible for the observed color change. The transposon insertion junctions were sequenced in one of the orange-colored mutants, and the adjacent sequence showed homology to several transactivators and repressors. Thus, if the transposon insertion is indeed responsible for the altered pigmentation, it is likely that the function of a regulatory gene was disrupted. Carotenoid biosynthesis pathways contain both structural and regulatory components (Armstong review; Perry, K et al; S. Liu 1986, J.Bact 168:607) and mutations in regulatory genes have been demonstrated to result in altered carotenoid accumulation and subsequent changes in pigmentation (Penfold R and Pemberton J, 1991, Curr. Microbiol. 23:259).

As an additional measure of the utility of the transposon library, we screened for and quite readily found mutants with reduced or absent capsule. Like many bacteria, including *Streptococcus, E. coli* and *Mycobacteria,* the capsule *R. equi* is predominately composed of polysaccharide.

We also screened for insertion mutants that were unable to grow on minimal salts media; and in so doing we identified a riboflavin auxotroph. This mutant contains an insertion in an ORF with extensive homology to the bifunctional protein containing GTP cyclohydrase II and 3,4-dihydroxy-2-butanone-4-phosphate synthase activities, components of the riboflavin biosynthesis pathway. We confirmed that the mutant could be rescued on minimal media if exogenous riboflavin was added. In general, wildtype *R. equi* grows poorly on minimal media, but the riboflavin auxotroph grows not at all; and supplementation with riboflavin will allow growth equivalent to that of the wildtype prototroph.

Riboflavin (vitamin B2) is the precursor of the coenzymes flavin mononucleotide phosphate (FMN) and flavin adenine dinucleotide phosphate (FAD), compounds essential for growth and cell division. Riboflavin is synthesized by plants, fungi and bacteria but not by higher eukaryotes. Some bacteria are readily able to make use of exogenous sources of riboflavin (ref *Bacillus*), but a number, for example *E. coli* and other *Enterobacteriaceae* lack a transport system for riboflavin uptake and thus, are unable to efficiently utilize environmental sources of riboflavin. In fact, riboflavin auxotrophs of *E. coli* were only relatively lately identified largely because exogenous supplementation necessitates very high concentrations of the vitamin and thus, the mutants were likely missed in initial screens. Even if a bacterium is in possession of an adequate uptake system, the mammalian environment may be so limiting in riboflavin availability that bacterial growth is prevented. Such a scenario was documented by studies of the veterinary pathogen *Actinobacillus pleuropneumoniae*, in which a riboflavin auxotroph was demonstrated to be incapable of causing disease in swine. Thus, we were interested to know whether our riboflavin mutant would be similarly attenuated in vivo. To access the virulence of the mutant strain we used a murine challenge model. Although immunocompetent mice are relatively resistant to *R. equi* infection, virulent strains of the bacteria will replicate in the early days post-infection, whereas attenuated strains will not. Furthermore, the ability to replicate in the tissues of the mouse has been demonstrated to correlate with the ability of *R. equi* to cause disease in foals. Therefore we infected mice with both virulent prototrophic *R. equi* and a similar number of the riboflavin mutant and monitored the in vivo grow of both strains, and discovered that riboflavin auxotrophy is indeed attenuating to *R. equi*. This is the first demonstration of an attenuation of *R. equi* due to a disruption of a metabolic gene. As auxotrophic mutants in other bacterial systems have been exploited as live-attenuated vaccine candidates, we are interested in examining the immunizing capabilities of the *R. equi* riboflavin auxotroph in the hopes of developing a vaccine strain to protect foals against rhodococcal disease. Furthermore, we are interested in studying other attenuating mutations, and we are now in a position to apply additional transposon-mediated approaches, such as signature-tagged mutagenesis, to identify molecules and pathways necessary for *R. equi* virulence.

By allelic exchange we made a mutation in a virulent strain of *R. equi* that removes a 7908 base-pair size region of the virulence plasmid. This deletion removes 5 genes belonging to the Vap (for virulence associated protein) family, specifically vapA, vapC, vapD, vapE and vapF and four unknown ORFs; we refer to this mutant as the vap locus mutant. We have confirmed by both PCR and Southern analysis that this region was indeed deleted. To assess the virulence of the mutant strains we used a murine challenge model of *R. equi* infection. Although immunocompetent mice are relatively resistant to *R. equi*, virulent strains of the bacteria will replicate in the early days post-infection, whereas attenuated strains will not. Furthermore, the ability to replicate in the tissues of the mouse has been demonstrated to correlate with the ability of *R. equi* to cause disease in foals. Therefore we infected mice with both virulent *R. equi* and a similar number of the vap locus mutant and monitored the in vivo grow of both strains. We discovered that the locus mutant was indeed attenuated in *R. equi*. It failed to replicate at all, and clearance began immediately post challenge. To determine which deleted gene or genes was responsible for the attenuation, we complemented the locus mutant with each gene individually. That is, we added back to the mutant each individual gene in the absence of the others. We found that by complementing with vapA alone, we were able to restore full virulence to the mutant in the murine model system.

Complementation with either vapC, vapD, vapE, or vapF had no effect, and the locus mutant was still attenuated. Thus, it seemed like the loss of vapA was the reason for the attenuation. To provide further proof that vapA was a virulence determinant, we decided to delete vapA alone from virulent wildtype *R. equi*. We did this by allelic exchange and likewise confirmed the deletion by PCR and Southern analysis. We infected mice with the vapA mutant and as expected the mutant was attenuated and did not grow in mice. Complementation of the vapA mutant with wildtype vapA restored virulence to the strain, providing final evidence that vapA is indeed a virulence determinate of *R. equi*. This is the first definitive demonstration of any virulence determinate in *R. equi*. As these two strains are attenuated, they hold potential for use as live-attenuated vaccine candidates to protect foals, pregnant mares and humans against rhodococcal diseases.

Virulence plasmid positive strains of *R. equi* express a 15-17 kDa protein corresponding to VapA (for virulence associated protein A). VapA is a highly immunogenic protein which is abundantly expressed. Its extracellular location is in consonance with the presence of a signal peptide at the amino terminal of the immature protein. Its expression is temperature and pH regulated, occurring maximally between 34° to 41° C. and at a pH of 5.0, thus resembling the virulence plasmid gene expression patterns of pathogenic *Yersinia* and *Shigella* species. Prior immunization of mice with VapA results in enhanced clearance from livers and spleens of mice challenged intravenously with *R. equi*. Similarly mice administered a high dose of antibodies to VapA enriched antigens are completely protected against intraperitoneal infection of *R. equi*. Foals with rhodococcal disease develop high antibody titers to VapA and exogenous administration of hyperimmune serum to foals appears to protect them against the disease. All these observations point to an important role of VapA in the virulence of *R. equi* although there is no direct evidence to support this premise. VapA exhibits no sequence similarity to any proteins in the databank and its function is still unknown. Virulence plasmid negative strains of *R. equi* do not express VapA and are incapable of causing disease in foals. However, expression of vapA on a multicopy plasmid in such strains does not restore their virulence. Thus we sought to determine whether vapA was a true determinate of virulence and if so, could disruption of vapA create an attenuated strain that might be useful as a vaccine.

Recently, the complete DNA sequence of the virulence plasmid of *R. equi* was determined. The plasmid contains 64 annotated open reading frames (ORFs) and can be divided into 3 broad regions viz. pathogenicity island, conjugation region and replication and partition region. The pathogenicity island is comprised of a total of 26 ORFs and a striking feature is the presence of 7 vap genes namely vapG, vapH, vapA, vapC, vapD, vapE and vapF spanning a 19 kb region. Interestingly, vapG and vapH are present as individual genes while others are clustered within approximately 8 kb region in pathogenicity island of the virulence plasmid. The proteins encoded by these genes exhibit significant sequence conservation especially in their second halves. Given the extensive sequence similarity among various Vap proteins, we sought to address their function in the virulence of *R. equi*, and reasoned that due to their shared homology, they may have overlapping function. If they did have redundant function, then deleting one might have no effect on virulence. Thus we constructed a mutant lacking the 8 kb DNA region encompassing vapA, vapC, vapD, vapE and vapF (Locus mutant). The results of analysis of this locus mutant led us to construct a second mutant in which only vapA was deleted (VapA mutant). We show that both mutants are incapable of multiplication in mice and are cleared rapidly in comparison to the wild type strain. Our results are the first demonstration of the role of VapA in R. equi virulence.

Of particular note, is that there is no preventative anti-R. equi vaccine. We hope that the live attenuated strains we have created will have immunizing potential. We are very interested in examining them for their ability as vaccines to prevent R. equi disease in foals.

The present invention encompasses not only methods for making attenuated R. equi mutants, but also the mutants themselves, host cells infected with the mutants and progeny mutants produced by these host cells. Antibody can be made to the attenuated mutant bacteria by infecting animals, preferably horses, at an effective dosage. Antibodies made in this manner are part of the invention and can be isolated and used in diagnostic procedures, or for detecting the presence of *R. equi* in cell culture.

One can create other mutants of the riboflavin or vapA genes, and test the resulting mutants for virulence to determine if the mutant represents an attenuated strain. By "attenuated" is meant a reduction in the severity, virulence or vitality of the disease causing agent. When an avirulent strain is obtained, it can then be utilized as a live vaccine.

Preparation of Vaccines.

Live Vaccine.

Bacteria for the live vaccine can be grown in the appropriate medium (supplemented with riboflavin in the case of riboflavin mutants) 37° C., to an $O.D._{600}$ of 0.8-1.5. Bacteria are then harvested, washed once in phosphate buffered saline (PBS), pH 7.0, diluted in phosphate buffered saline (PBS) or PBS containing 5 μg/ml riboflavin to the appropriate cell density, and used immediately as vaccine.

Formulation of Vaccines.

The attenuated strains can be raised in Brain Heart Infusion (BHI) (Difco Laboratories) (Detroit, Mich.) broth. Other media known in the art can, however, be used. Cultures are typically begun by inoculation from single colonies of organisms confirmed to be mutants.

For vaccine administration, the attenuated bacteria are typically combined with a pharmaceutically acceptable carrier appropriate for the intended mode of administration. Pharmaceutical compositions include a unit dose of the attenuated bacteria in combination with a pharmaceutically acceptable carrier and, in addition, can include other medicinal agents, pharmaceutical agents, carriers, adjuvants, diluents, and excipients. The proportion of attenuated bacteria and adjuvant can be varied over a broad range so long as both are present in effective concentrations as described below. The vaccine compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

The invention is compatible with various excipients and adjuvants, and these can be incorporated into preparations as desired. For example, vaccine compositions of the present invention can be formulated following accepted convention using standard buffers, carriers, stabilizers, diluents, preservatives, and solubilizers, and can also be formulated to facilitate sustained release. Diluents can include water, saline, dextrose, ethanol, glycerol, and the like. Additives for isotonicity can include sodium chloride, dextrose, mannitol, sorbitol, and lactose, among others. Stabilizers include albumin, among others. Non-limiting examples of adjuvants include the RIBI adjuvant system (Ribi Inc.), alum, aluminum hydroxide gel, oil-in-water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), or other saponin fractions, monophosphoryl lipid A, Avridine lipid-amine adjuvant, heat-labile enterotoxin from *E. coli* (recombinant or otherwise), cholera toxin, or muramyl dipeptide, among many others. The vaccine can further comprise one or more other immunomodulatory agents such as, e.g., interleukins, interferons, or other cytokines.

Examples of pharmaceutically acceptable carriers include solutions such as normal saline, Ringer's solution, PBS (phosphate-buffered saline), and generally mixtures of various salts including potassium and phosphate salts, with or without sugar additives such as glucose. Suitable carrier solutions also include, for example, water, dextrose, glycerol, or buffered vehicles. Nontoxic auxiliary substances, such as wetting agents, buffers, or emulsifiers may also be added to the composition. Adjuvants are generally commercially available from various sources.

Administration of the Vaccines

The pharmaceutical compositions of the invention can be administered by any suitable means, e.g., parenterally (subcutaneously, intramuscularly, or intraperitoneally), intravenously, nasally or orally. Injectables can be prepared in conventional forms. An appropriate evaluation of the time and method for delivery of the vaccine is well within the skill of the veterinarian or clinician.

Vaccine compositions of the invention are administered to humans and other mammals susceptible to or otherwise at risk of infection to elicit an immune response against the bacteria and thus enhance the patient's own immune response capabilities. Such an amount is defined to be an immunogenically effective amount. The exact amount of such pharmaceutical compositions required will vary from subject to subject, depending on the species, age, weight and general condition of the subject, the particular bacteria used, the mode of administering it, the nature of the formulation, and the like. The judgment of the prescribing physician is also an important consideration. Generally, dosage will approximate that which is typical for the administration of other live attenuated vaccines (see, e.g., Ravn et al., *J. Immunol.* 158:1949-1955 (1997) (administration to humans); Chambers et al., *J. Immunol.* 158:1742-1780 (1997) (administration to mice); Roia, F. "Immunizing Agents and Diagnostic Skin Antigens", in Gennaro, A., ed., *Remington's Pharmaceutical Sciences,* Mack Publishing Company, Easton, Pa. (17th ed., 1985 and 18th ed., 1990) (the entirety of both of these editions of Remington's are hereby incorporated by reference).

Natural infections are believed to occur from exposure to as few as 1 to 10 organisms. Clearly, however, the chances of becoming infected go up the number of organisms increases, although there can be expected to be a point of diminishing returns. For purposes of vaccination, the number of attenuated bacteria for an aerosol administration can range from 1 to as many as about $10^6$ cells per dose.

Preferably, the number of cells administered will range between about $10^2$ and about $10^4$ cells per dose, and more preferably are between about $10^2$ and about $10^3$ cells per dose. For parenteral administration, the number of cells can also range from about 1 to about $10^6$ cells per dose, with about $10^4$ cells per dose being preferred. For oral administration, the dose range is preferably about $10^4$ to about $10^7$ cells, with doses on the lower end of the range being preferred. A suitable dose size is about 0.1-5.0 ml, preferably about 0.1-1.0 ml. Accordingly, a typical dose for aerosol administration for example, would comprise 0.1 to 0.5 ml containing about $1\times10^3$ cells, or for subcutaneous administration, 0.1 to 0.5 ml containing about $1\times10^4$ cells.

The timing of administration of the vaccine and the number of doses required for immunization can be determined from standard live attenuated vaccine administration protocols. Typically, this vaccine composition will be administered in one dose (see, e.g., Product Information, *Physicians Desk Reference* (1996); Remington's, supra).

Lyophilization of the bacterial cells, and resuspension in a sterile solution prior to administration is will be a preferred embodiment of the invention in countries in which availability of refrigeration in the field or rural areas may be problematic, and is likely to be preferred in this country where ease of storage is desired. Frozen aliquots of vaccine, which can be thawed and injected without the need for resuspension, are likely to be preferred where these two factors are not major concerns since freezing results in better viability of the organisms than does lyophilization.

Immunization procedures can be optimized using procedures well known in the art. A single dose can be administered to animals, or, alternatively, two or more inoculations can take place with vaccine separated by intervals of two to ten weeks.

If desired, sera can be collected from the inoculated animals and tested for the presence of antibodies to *R. equi*.

The terms "induction of an immune response," and the like, are used broadly herein to include the induction of, or increase in, any immune-based response in the organism in response to vaccination, including either an antibody or cell-mediated immune response, or both, that serves to protect the vaccinated organism against *R. equi*. The terms "protective immunity," "protective immune response" and "protect," as used herein, are not limited to absolute prevention of *R. equi* diseases in mammals, or absolute prevention of infection of mammals by *R. equi*, but are intended to also refer to any reduction in the incidence or severity, as determined by a veterinarian, of infection by the pathogen, or incidence or severity of the disease or any symptom or condition resulting from infection with the pathogen as compared to that occurring in an unvaccinated, infected control animal.

EXAMPLES

Example 1

Bacterial Strains

*R. equi* strain 103+ was originally isolated from a foal with *R. equi* pneumonia, and was kindly provided by J. Prescott (Guelph, Ontario). Standard culture media was Brain Heart Infusion (BHI) (Difco Laboratories) (Detroit, Mich.) broth or agar and unless otherwise noted, growth was done at 30° C. to maintain the presence of the *R. equi* virulence plasmid. Antibiotics when needed were used at the following concentrations: Apramycin (80 mg/ml), Hygromycin (180 mg/ml). Culture of the riboflavin auxotroph on minimal media required the addition of 200 µg/ml of riboflavin. To restore color to the pyruvate kinase mutant, pyruvic acid (Sigma) (St. Louis, Mo.) (10 mg/ml final concentration) was added to the media. To restore growth of the riboflavin auxotroph on minimal media, riboflavin (Sigma) was added at a final concentration of 200 µg/ml. Electrocompetent *R. equi* 103+ was created by growth in BHI at 30° C. to an $O.D._{600}$ of 0.8-1.5. The culture was pelleted at 4° C., washed twice with cold $dH_2O$ and finally resuspended in ½0 the original culture volume in cold $dH_2O$ with 10% glycerol. Aliquots of 400 □l were then stored at −80° C. Electroporation was performed in 2 mm cuvettes, at 2.5 Kv, 720 Ohms using 400 µλ of thawed cells. Electroporated bacteria were recovered for 1 h in BHI supplemented with 5M sucrose.

Example 2

Construction of Transposon Delivery Plasmid pMV261H, a *Mycobacteria-E. coli* shuttle plasmid, was cut with AgeI in order to isolate a 2735 bp fragment containing a hygromycin resistance gene and an *E. coli* origin of replication (oriE). This AgeI fragment was then ligated to AgeI digested pSC171.2 to create pJA103.2. pSC171.2 is an *E. coli* vector which contains a multicloning site flanked by the inverted repeats of the Himar1 mariner transposon. Cloning at the AscI site of pSC171.2 placed the hygromycin resistance gene and the oriE inside of the transposon inverted repeats. Subsequent FspI/SapI digestion of pJA103.2 was done to yield a 3300 bp fragment containing the newly constructed hygromycin marked, oriE containing Himar1 mini-transposable element. The FspI/SapI transposon fragment was blunted and ligated to NsiI/BciVI digested and blunted pSC146 to create the ts transposon delivery vector pJA2.2. pSC146 is a *Mycobacteria-E. coli* shuttle plasmid which contains a temperature sensitive version of the pAL5000 myocobacterial origin of replication (oriM) (Guilhot C, Gicquel B and Martin C, 1992 FEMS Micro Letters 98:181). pSC146 also contains the mariner transposase gene and an apramycin resistance gene. The NsiI/BciVI digestion of pSC146 removed the oriE from the backbone of this plasmid so that ligation to the transposon-containing fragment produced a product (pJA2.2) with a single oriE situated between the inverted repeats of the transposon.

Example 3

Transposon Mutagenesis pJA2.2 (~180 ng) was electroporated into competent *R. equi*, and plated on BHI supplemented with hygromycin (180 µg/ml) and cultured at 30°C. for three days. Plates were then scraped and the bacteria suspended in 20 mls BHI. From this suspension, 100 □-l aliquots were replated on BHI with hygromycin and incubated at the non-permissive temperature of 42° C. for three days to cure the transposon delivery vector. Transposon insertions mutants were identified by picking and patching of individual colonies onto BHI supplemented with hygromycin and BHI supplemented with apramycin. Clones that were hygromycin resistant, but apramycin sensitive, were deemed positive for transposition. Further confirmation of transposon insertion was attained by PCR analysis of positive clones for both the presence of the transposon and the absence of the apramycin resistance gene. The forward primer 5'-TTCACCGATCCGGAG-GAACT-3' (SEQ ID NO: 1) and the reverse primer 5'-TC-CCCGGTCTCTAGAATTCA-3' (SEQ ID NO: 2) were used to amplify a 472 bp fragment of the transposon. To attempt to amplify the aprimycin gene the forward primer 5'-TCATCGGTCAGCTTCTCAAC-3' (SEQ ID NO: 3) and the reverse primer 5'-CACAGCAGTGGTCATTCTCG-3' (SEQ ID NO: 4, were used. Southern blotting was also done to confirm single insertion of the transposon within an individual clone. Briefly, in order to isolate total nucleic acids, a 6 ml overnight culture of the clone of interest was pelleted and resuspended in 500 µl of 10 mM Tris 1 mM EDTA (TE) pH 8.0 with 100 µg/ml of lysozyme. After a 3 to overnight incubation at 37° C., 70 µl SDS and 6 µl of 10 mg/ml Proteinase K (final concentration 100 µg/ml) was added and a 1 h incubation at 65° C. was done. Next 100 µl of 5M NaCl was added, the solution gently mixed, then 80 µl of 10% hexadecyltimethyl ammonium bromide (CTAB) in 0.7M NaCl was added and the mixture incubated for 20 min at 65° C. followed by a phenol:chloroform:isoamyl alcohol extraction. DNA was precipitated using 0.6 volume of 100% isopropanol. DNA from positive clones was digested with XmaI, which does not cut within the transposon, and then run on a 1% agarose gel. Blots were probed with a purified (472 bp) PCR fragment of the transposon labeled using the ECL direct nucleic acid labeling kit. Processing of the gel, probe labeling, and detection was carried out according to manufacturers recommendations.

Example 4

Morphology Screen

The transformed R. equi library was plated on BHI agar supplemented with hygromycin and placed at 42° C. for three days. Plates were then placed at 30° C. for two days to allow the clones to grow large enough to examine. Some of the clones that showed significant morphological changes such as alterations in color or capsule, were picked and patched onto BHI agar with hygromycin and BHI agar with apramycin. Those clones that were hyg$^r$, apr$^s$ were analyzed by colony PCR to confirm the presence of transposon insert, loss of the donor plasmid apramycin gene, and the presence of vapA indicating maintenance of the R. equi virulence plasmid. To amplify the vapA the forward primer 5'-GGCGTCGCTGGGCCCACCGTTCTTG-3' (SEQ ID NO: 5) and the reverse primer 5'-TACGTGCAGCGAAT-TCGGCGTTGTGC-3' (SEQ ID NO: 6) were used.

Example 5

Auxotrophy Screen

From the same plates used for the morphology screen, additional clones were picked and patched onto BHI with hygromycin and onto minimal media with hygromycin. Minimal salts media was composed of 30 mM $K_2HPO_4$, 16.5 mM $KH_2PO_4$, 78 mM $(NH_4)_2SO_4$, 0.85 mM sodium citrate, 1 mM $MgSO_4$, 0.02% glycerol, and 0.0016% thiamine. Clones that grew on BHI but not on minimal media, were further analyzed by PCR, as above, to confirm presence of vapA and the transposon and to document the loss of the apramycin gene.

Example 6

Sequencing

R. equi clones to be sequenced were inoculated into 6 ml BHI with hygromycin and grown overnight at 37° C. Cultures were then pelleted for genomic DNA isolation as described above. To recover the R. equi insertion site, genomic DNA was digested with XmaI, self-ligated and then electroporated into E. coli strain DH10B (Gibco BRL) (Grand Island, N.Y.) according to manufacturers instructions. The transformed E. coli was plated onto LB (Difco) agar with hygromycin (180 µg/ml). Plamid DNA containing the R. equi transposon insertion was isolated from E. coli by Nucleospin (Clonetech) (Palo Alto, Calif.) mini-prep procedure and submitted for sequencing at the Microbiology Core Sequencing Facility (Harvard Medical School). Sequencing from the transposon ends was done with the outward directed primer pairs 5'-ATCATCAGGGCTCGACGGGA-3' (SEQ ID NO: 7) and 5'-CAAGTTGTCCTCGCT-GC-CAC-3' (SEQ ID NO: 8) or primer pairs 5'-GCTCTTAGCG-GCCCGGAAA-CGTCCTCGAAA-3' (SEQ ID NO: 9) and 5'-CTTGGCCATTGCGAAGTGATT-CCTCCGGAT3' (SEQ ID NO: 10).

Example 7

Mouse Infection

Female BALB/cJ mice were obtained from Jackson Laboratories (Bar Harbor, Me.) and infected at approximately 8 weeks of age. Titered frozen aliquots of the bacterial strains were thawed, cultured for 1 h at 37° C., then pelleted and diluted in phosphate buffered saline (PBS). Even though the frozen bacterial aliquots had been titered previously, the titer of the inoculum was reconfirmed at the time of injection by dilution plating of the injection stock. Groups of mice were injected intravenously in the tail veins with $3-7\times10^5$ CFU of wildtype R. equi 103+ or the riboflavin auxotroph in 100 µl PBS. In order to monitor bacterial clearance or growth, at various times post-injection, 4 mice from each experimental group were sacrificed and their spleens, livers, and lungs were aseptically removed. Each organ was placed in PBS with 0.05% tween-80 and disrupted using a Stomacher-80 apparatus (Tekmar, Cinncinati, Ohio). Serial 10-fold dilutions of the tissue homogenate were plated onto BHI agar supplemented with riboflavin and/or antibiotic when appropriate. Plates were incubated at 37° C. Colony forming units (CFU) were determined 36 h later.

Example 8

In Vivo Transposition in R. equi

Because transposons belonging to the mariner family have been shown to transpose randomly in a variety of organisms including insects, protozoa and bacteria (Plasterk R et al TIG 1999), we decided to use the Himar1 element as the foundation upon which to build a mutagenesis system for the actinomycete R. equi. However, we first had to work out a means to deliver the mini-transposon to R. equi. We ultimately developed a delivery protocol that involved use of a plasmid with a temperature sensitive origin of replication. We had previously determined that the mycobacteria pAL5000 origin of replication (oriM) could function to maintain an episomal plasmid in R. equi (Giguere and Hondalus). We next confirmed that an oriM-based replicon could be retained even in the presence of the *R. equi* virulence plasmid. In other words, the two plasmids were not incompatible. We then sought to determine if a temperature sensitive (ts) version of the pAL5000 (Guihot C, Martin C FEMS Micro Letters; Pelicic V, Jackson et al 1997, PNAS, 94:10955) was likewise ts in *R. equi*. Therefore, we transformed the virulent *R. equi* strain 103+ with a mycobacteria-*E. coli* shuttle plamid (pSC146) containing the ts oriM, and transformants were selected at 30° C. (permissive temperature). To determine if the oriM in pSC146 was likewise ts in *R. equi*, we scraped the transfomants from the plates held at 30° C. and re-plated duplicate dilutions of the transformed bacteria, incubating a set of plates at 30° C. and at 42° C. (non-permissive temperature), a temperature that is not lethal to the bacterium. We observed a several hundred-fold reduction in the number of transformed bacteria at 42° C. as compared to 30° C., indicating that the oriM was indeed ts in *R. equi*, able to function at 30° C. but not at 42° C. Therefore, we used pSC146 as the backbone vector to create our mini-transposon delivery vehicle.

To generate insertion mutants, we constructed the delivery plasmid, pJA2.2 which contains the Himar1 transposase, ts oriM, and apramycin resistance genes located on the backbone, as well as a Himar1 minitransposon element containing a hygromycin resistance cassette and an *E. coli* origin of replication (oriE) located within the inverted repeats. This was the only *E coli* origin of replication on the delivery plasmid and its presence facilitated recovery of the transposon insertions. PJA2.2 was introduced into *R. equi* 103+ by electroporation. Transformants were selected on hygromycin plates at 30° C., a temperature allowing plasmid replication and transposition. Transformants were then scraped off the plates, resuspended in media and aliquots re-plated and incubated at either 30° C. (to determine the number of transformants) or 42° C., a temperature at which the delivery plasmid cannot replicate. Plates that were incubated at 42° C. had approximately 4-6000-fold fewer colonies than the plates incubated at 30° C. All of the colonies that arose at 42° C. were hygromycin resistant and PCR analysis determined that this resistance correlated with the presence of the transposon. 98% the clones surviving at 42° C. were sensitive to apramycin, indicating loss of the delivery plasmid, since the apramycin resistance gene was on the vector backbone and not contained within the transposon. Using this method, we obtained approximately 6000 hygromycin resistant mutants, and could have easily obtained more, had we increased the amount of transformants plated and incubated at 42° C. Southern blot analysis of 50 randomly chosen insertion mutants determined that 98% (49 out of 50) contained a single transposon insertion. Genomic DNA from the *R. equi* insertion mutants was isolated and digested with XmaI, an enzyme that cuts frequently within *R. equi* DNA but not within the transposon. Blots were probed with a 472 bp PCR fragment of the Himar1 element. Single insertion mutants display one band upon Southern blotting whereas multiple bands would be seen in clones containing more than one insertion.

In order to more thoroughly characterize the composition of the *R. equi* transposon mutant library, we sequenced the insertion junctions of 100 randomly chosen mutants. Transposon insertions were recovered by self-ligating XmaI genomic digests of individual clones and electroporation of *E. coli* cells with selection on hygromycin media. Plasmids containing the transposon and flanking insert DNA were subsequently isolated from *E.coli* and submitted for sequencing. Of the 100 clones examined, 88 unique insertion sites were identified. Five of the 100 clones sequenced were not insertions but rather represented delivery plasmid JA2.2 that had survived the non-permissive selection. Eight of the clones were identified twice and thus, likely represented siblings. 24 insertions occurred in DNA sequences with no significant homology to anything in the data bases. Several insertions (40) were within sequences displaying the highest degree of homology to *Mycobacteria* spp., including *M. tuberculosis, M. leprae* and *M. smegmatis*. As has been reported for other mariner elements, all insertions occurred at a TA dinucleotide and no other insertion concensus sequence was recognized. Some slight target bias was seen as two regions of sequence were identified more than once, specifically the ORF of a putative penicillin binding protein was hit 3 times, albeit at unique sites and a probable ribosomal RNA gene was twice identified, although once again each insertion was distinct.

Example 9

Selection of Morphological Mutants

We reasoned that if the Himar1 element did indeed insert randomly within the *R. equi* genome it should be possible to readily identify mutants with insertions resulting in phenotypic changes in colony morphology. *R. equi* is normally salmon-pink in color due to the production of γ-carotene (Ichiyama et al 1989, Microbiol. Immunol). We thought it likely that among the mutants we would find clones with altered pigmentation. Out of 5756 transposon insertion mutants screened, we identified X non-pigmented, X yellow and X bright orange clones. A comparative screening of more than 12,000 wildtype *R. equi* colonies identified none with changed color. The mutant pigment phenotypes colors are in contrast to that of wildtype *R. equi*. Sequence analysis of the insertion junction of a yellow mutant determined that the transposon had disrupted an ORF with homology to a *Brevibacterium* phytoene desaturase gene, an enzyme involved in carotenoid biosynthesis. Similar insertion site analysis of an orange pigmentation mutant showed homology to several DNA repressors. Comparable sequencing of a white (non-pigmented) mutant determined that the transposon had inserted into an ORF with high homology to pyruvate kinase. To evaluate whether the transposon insertion in this clone was responsible for the observed non-pigmented phenotype, we plated the clone on BHI media supplemented with pyruvic acid (pyruvate). Indeed, the addition of pyruvate restored the wildtype, salmon-colored pigmentation to the mutant, data consistent with a transposon-linked phenotype.

As a further test of the utility of the *R. equi* transposon library, we also looked for mutants with alterations in mucoidicity. Owing to the presence of a polysaccharide capsule, wildtype *R. equi* is mucoid in nature. Out of the same mutant clones screened above, we noted 262 that appeared to be drier than that of wildtype *R. equi*. Once again, screening of over twice this number of wildtype colonies discovered none with apparent alterations in the character of the capsule. Insertion sequence analysis of one of the capsule mutants showed significant homology to the hexose monophosphate shunt enzyme gluscose-6-phosphate dehydrogenase or polyketide synthases. In a second dry mutant, the transposon had inserted into a region with high homology to mycolyl transferases of *Mycobacteria* spp. Polyketide synthases and mycolyl transferases are involved in lipid metabolism and mutations of these enzymes would be consistent with phenotypic changes in the bacterial cell wall.

Example 10

Identification of a Riboflavin Auxotroph

Because the ultimate goal of our work is to learn something of the pathogenesis of *R. equi* and to create attenuated strains of the bacterium that may be useful as vaccines, we decided to look for auxotrophic mutants of the organism. Auxotrophs are strains that require particular exogenous nutritional supplementation for growth, and they have demonstrated utility in a variety of bacterial systems as live-attenuated vaccines. Thus, we screened approximately 1000 *R. equi* transposon mutants and identified 10 that could grow on BHI media but not on minimal salts media. Three of these mutants were shown to have unique transposon insertions into an ORF with extensive homology to the bifunctional enzyme comprising a GTP cyclohydrolase and 3,4-dihydroxy-2-butanone-4-phosphate synthase (DHBP synthase), an enzyme in the biosynthesis pathway of the vitamin riboflavin. Subsequent supplementation of minimal salts media with riboflavin restored the growth of these mutants, a finding consistent with the hypothesis that transposon disruption of the riboflavin biosynthesis pathway was responsible for the auxotophic phenotype.

Example 11

Riboflavin Auxotrophy Attenuates Growth of *R. equi* In Vivo

Because riboflavin auxotrophy has been demonstrated to attenuate another pathogen, *Actinobacillus pleuropneumoniae*, we sought to determine whether the riboflavin auxotroph of *R. equi* would be similarly affected for growth in vivo. To test the effect of riboflavin auxotrophy on *R. equi* virulence, Balb/cJ mice were infected with the riboflavin mutant, and the clearance of the auxotroph was compared to that of wildtype *R. equi*. Although the mouse does not develop rhodococcal pneumonia, virulent (i.e., virulence plasmid-containing) strains of *R. equi* will replicate in vivo over the short-term, and this ability to replicate in the mouse has been correlated to virulence in foals (Giguere and Hondalus; Takai 1995 FEMS Immunol Med Microbiol. 11:181). In mice intravenously challenged with wildtype *R. equi*, the bacteria increase in number approximately 5-fold in the liver and 10-fold in the spleen during the first 48 hours post-challenge after which time the bacterial burden plateaus. Sometime around day 5 post-infection, clearance of the bacteria becomes apparent and bacterial numbers quickly decline. The infection is generally completely resolved by 14-21 days depending on the size of the initial inoculum. In contrast to the in vivo growth displayed by wildtype *R. equi*, the riboflavin auxotroph did not replicate. Rather, it persisted at challenge level for 4-5 days post infection, after which its numbers steadily declined at a rate similar to that of wildtype. We confirmed that the virulence plasmid was present in the riboflavin mutant, and therefore the observed attenuation of the strain cannot be attributed to plasmid loss. Thus, the inability of the mutant to synthesize riboflavin rendered it incapable of in vivo growth in a murine *R. equi* virulence model.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

---

The invention claimed is:

1. A mutant strain of *Rhodococcus equi* (*R. equi*), said mutant strain being a riboflavin auxotroph, and said mutant strain further having reduced pathogenicity relative to a wild type strain.

2. The mutant strain of *R. equi* of claim 1, said mutant strain comprising a transposon insertion in the gene encoding a dual function GTP cyclohydrolase/3,4-dihydroxy-2-butanone-4-phosphate synthase (DHBP synthase), said transposon insertion inactivating the function of DHBP synthase.

3. The mutant strain of claim 2, wherein said transposon comprises a Himar 1 transposable element.

4. A vaccine comprising the mutant strain according to claim 1.

5. The vaccine of claim 4 further comprising pharmaceutically acceptable carrier.

6. A method of making a genetically stable mutant *R. equi* strain, said method comprising inserting a transposon into the gene that encodes DHBP synthase.

* * * * *